United States Patent [19]

Andrews et al.

[11] Patent Number: 5,364,824

[45] Date of Patent: * Nov. 15, 1994

[54] CATALYSIS FOR THE PRODUCTION OF MALEIC ANHYDRIDE CONTAINING VANADIUM-PHOSPHORUS OXIDE WITH SELECTED PROMOTER ELEMENTS

[75] Inventors: William J. Andrews, Hazelwood; Jerry R. Ebner, St. Peters; Timothy R. Felthouse, St. Louis, all of Mo.

[73] Assignee: Huntsman Specialty Chemicals Corporation, Salt Lake City, Utah

[ * ] Notice: The portion of the term of this patent subsequent to Aug. 11, 2009 has been disclaimed.

[21] Appl. No.: 986,652

[22] Filed: Dec. 8, 1992

[51] Int. Cl.$^5$ .................. B01J 27/198; B01J 27/18; C07D 307/60
[52] U.S. Cl. .................. 502/209; 549/259; 549/260
[58] Field of Search ........................ 502/209

[56] References Cited

U.S. PATENT DOCUMENTS

| | | | |
|---|---|---|---|
| 3,478,063 | 11/1969 | Friedrichsen | 260/346.8 |
| 3,862,146 | 1/1975 | Boghosian | 260/346.8 A |
| 3,864,280 | 2/1975 | Schneider | 252/435 |
| 3,888,886 | 6/1975 | Young et al. | 260/346.8 |
| 3,905,914 | 9/1975 | Jurewicz et al. | 502/209 |
| 3,931,046 | 1/1976 | Weinstein et al. | 252/429 R |
| 3,980,585 | 9/1976 | Kerr et al. | 252/437 |
| 4,020,174 | 4/1977 | Partenheimer | 260/346.8 A |
| 4,043,943 | 8/1977 | Schneider | 252/437 |
| 4,049,574 | 9/1977 | Kerr et al. | 252/437 |
| 4,056,487 | 11/1977 | Kerr | 252/437 |
| 4,065,468 | 12/1977 | Grasselli et al. | 260/346.75 |
| 4,092,332 | 5/1978 | Freerks et al. | 260/346.75 |
| 4,105,586 | 8/1978 | Kerr | 252/437 |
| 4,108,874 | 8/1978 | Moviya et al. | 260/346.75 |
| 4,110,350 | 8/1978 | Umemura et al. | 260/346.75 |
| 4,132,670 | 1/1979 | Katsumoto et al. | 252/437 |
| 4,147,661 | 4/1979 | Higgins et al. | 252/435 |
| 4,151,116 | 4/1979 | Mc Dermott | 252/435 |
| 4,152,338 | 5/1979 | Kerr | 260/346.75 |
| 4,152,339 | 5/1979 | Kerr et al. | 260/346.75 |
| 4,153,577 | 5/1979 | Barone | 252/435 |
| 4,158,671 | 6/1979 | Barone | 260/546 |
| 4,172,084 | 10/1979 | Bremer | 260/346.75 |
| 4,187,235 | 2/1980 | Katsumoto et al. | 260/346.75 |
| 4,209,423 | 6/1980 | Hutchings et al. | 252/435 |
| 4,218,382 | 8/1980 | Milberger et al. | 260/346.75 |
| 4,219,484 | 8/1980 | Milberger et al. | 260/346.75 |

(List continued on next page.)

FOREIGN PATENT DOCUMENTS 0003431 8/1979 European Pat. Off. .
0098039 5/1983 European Pat. Off. .
0092619 11/1983 European Pat. Off. .

OTHER PUBLICATIONS

Tamaki et al, Chemistry Letters, pp. 13–16 (1992).
Sanares et al, Catalysis Today, 15, pp. 527–535 (1992).
Hutchings, Applied Catalysis, 72, pp. 1–32 (1991).
Ai, Applied Catalysis, 28, pp. 223–233 (1986).

*Primary Examiner*—Paul E. Konopka
*Attorney, Agent, or Firm*—Constance S. Huttner; Evelyn M. Sommer; Walter Scott

[57] ABSTRACT

A phosphorus vanadium oxide catalyst for the oxidation of a $C_4$ hydrocarbon. The catalyst comprises a shaped body having a volume, or a fixed bed comprising shaped bodies having an average volume, of at least about 0.02 cc, and contains a promoter selected from among Bi, Sb, Ge, Ti, Zr, La, Ce, Ni, Zn, U, Sn, Si or mixtures thereof. The promoter is present in a proportion that enables the catalyst to have a developed surface area of at least about 28 $m^2/g$, and to exhibit a weight/area productivity of at least about 3.5 mg maleic anhydride/$m^2$-hr and/or a weight/weight productivity of at least about 100 g maleic anhydride/kg.cat.-hr. when contacted with a gas containing 2.4% by volume n-butane in air, at a gas flow volume to catalyst weight ratio of 2180 cc/g-min., under a pressure of $1.055 \times 10^2$-kPa-G, and at a temperature sufficient to maintain a hydrocarbon conversion of 85 mole percent. Methods for the preparation of the catalyst include activation by ANST.

21 Claims, No Drawings

U.S. PATENT DOCUMENTS

| | | | |
|---|---|---|---|
| 4,222,945 | 9/1980 | Higgins et al. | 260/346.75 |
| 4,225,465 | 9/1980 | Bremer | 252/435 |
| 4,244,878 | 1/1981 | McDermott | 260/346.75 |
| 4,251,390 | 2/1981 | Barone | 252/435 |
| 4,283,307 | 8/1981 | Barone et al. | 252/432 |
| 4,288,372 | 9/1981 | Hutchings et al. | 260/346.75 |
| 4,292,201 | 9/1981 | Vartuli et al. | 252/435 |
| 4,317,777 | 3/1982 | Higgins et al. | 260/346 |
| 4,328,120 | 5/1982 | Udovich | 252/435 |
| 4,337,173 | 6/1982 | Otake | 252/435 |
| 4,351,773 | 9/1982 | Milberger et al. | 549/259 |
| 4,371,702 | 2/1983 | Bither, Jr. | 549/260 |
| 4,396,535 | 8/1983 | Bremer et al. | 252/435 |
| 4,400,522 | 8/1983 | Lemanski et al. | 549/260 |
| 4,442,226 | 4/1984 | Bither, Jr. | 502/209 |
| 4,448,893 | 5/1984 | Bremer et al. | 502/209 |
| 4,456,764 | 6/1984 | Wrobleski | 549/260 |
| 4,465,846 | 8/1984 | Bremer et al. | 549/260 |
| 4,525,471 | 6/1985 | Bremer et al. | 502/209 |
| 4,560,674 | 12/1985 | Wrobleski et al. | 502/209 |
| 4,562,268 | 12/1985 | Wrobleski et al. | 549/259 |
| 4,567,158 | 1/1986 | Wrobleski et al. | 502/209 |
| 4,604,371 | 8/1986 | Moorehead | 502/60 |
| 4,632,916 | 12/1986 | Bither, Jr. | 502/209 |
| 4,639,530 | 1/1987 | Moorehead | 549/260 |
| 4,649,205 | 3/1987 | Edwards et al. | 549/260 |
| 4,699,985 | 10/1987 | Bither, Jr. | 549/260 |
| 4,732,885 | 3/1988 | Edwards et al. | 502/209 |
| 4,748,140 | 5/1988 | Blum et al. | 502/209 |
| 4,782,166 | 11/1988 | Moorehead | 549/260 |
| 4,784,981 | 11/1988 | Heinz-Jurgen | 502/209 |
| 4,801,567 | 1/1989 | Moorehead | 502/77 |
| 4,801,569 | 1/1989 | Desmond et al. | 502/209 |
| 4,824,819 | 4/1989 | Edwards et al. | 502/209 |
| 4,950,769 | 8/1990 | McCandless et al. | 549/257 |
| 4,957,894 | 9/1990 | Haddad et al. | 502/209 |
| 4,965,235 | 10/1990 | Haddad et al. | 502/209 |
| 4,996,179 | 2/1991 | Haddad et al. | 502/209 |
| 5,093,298 | 3/1992 | Haddad et al. | 502/209 |
| 5,095,125 | 3/1992 | Haddad et al. | 549/259 | ns as

CATALYSIS FOR THE PRODUCTION OF MALEIC ANHYDRIDE CONTAINING VANADIUM-PHOSPHORUS OXIDE WITH SELECTED PROMOTER ELEMENTS

BACKGROUND OF THE INVENTION

This invention relates to novel catalysts for the selective vapor phase oxidation of a nonaromatic hydrocarbon to maleic anhydride and processes for the manufacture of these catalysts. The catalysts of this invention exhibit improved activity for the conversion of nonaromatic hydrocarbons resulting in lower temperature operations while maintaining excellent selectivity to maleic anhydride. Common chemical feedstocks include nonaromatic hydrocarbons such as n-butane, 1- and 2-butenes, 1,3-butadiene and mixtures thereof.

Maleic anhydride is produced throughout the world as a valuable chemical intermediate that finds use in unsaturated polyester resins, lubricating additives, agricultural chemicals, copolymers, and in the production of fumaric and maleic acids.

DESCRIPTION OF THE PRIOR ART

Procedures for the preparation of catalysts comprised of vanadium-phosphorus oxide are disclosed and taught in the prior art. Many references teach that it is preferable to reduce the vanadium to the tetravalent state in solution. Such catalysts are prepared by contacting vanadium and phosphorus compounds under conditions where substantial reduction to the tetravalent state of vanadium occurs to form the catalyst precursor. In many instances, promoter elements are also included in the catalyst precursor. The catalyst precursor is recovered, dried, and calcined to produce the catalyst.

It is generally recognized that the most desirable catalysts contain a substantial proportion of vanadyl pyrophosphate, a compound represented by the formula $(VO)_2P_2O_7$ whose X-ray diffraction pattern exhibits its primary peaks at d-spacings of 3.86, 3.14 and 2.98 Å. Numerous references in the patent and open literature also discuss the incorporation of various metals as promoters in vanadium phosphorus oxide catalysts. A very wide variety of metals has been proposed for such purpose, and data have been published indicating a beneficial effect on yields or selectivity. Most of the literature does not speculate on how the promoters operate to enhance catalyst performance. However, some theories have been advanced. A survey article by Hutchings, "Effect of Promoters and Reactant Concentration on the Selective Oxidation of n-Butane to Maleic Anhydride Using Vanadium Phosphorus Oxide Catalysts," *Applied Catalysis* 72(1991), pp. 1–32 suggests that promoters serve a two fold function: to enable the formation of required vanadium phosphorus oxide ("VPO") compounds while decreasing the formation of deleterious phases; and to enable the formation of solid solutions which regulate the catalytic activity of the solid phase. Hutchings reports that promoter to vanadium molar ratios of 0.15 to 0.20 are considered to provide optimum results, though one study is adverted to in which favorable results were obtained with an Mo/V ratio of 0.04. Hutchings further reports that Bi, Cd, Co, Cu, Li, Mg, U, Zn and Zr appear to form phosphates with excess phosphorus present, thereby preventing formation of inactive or deleterious VPO compounds, such as $VO(H_2PO_4)_2$.

The Hutchings article further notes that the impregnation of a VPO catalyst with a promoter may increase the surface area. However, this reference does not mention, or indicate any significance to, the point at which surface area is measured. Nor does it suggest an effect of a promoter on the surface area of the catalyst. Most of the article concentrates on the reported effect of various promoters on the specific activity of a catalyst of a given area.

Ai, "Effects of Preparation Variables on the Properties of $V_2O_5$-$P_2O_5$-$ZrO_2$ Catalysts for the Oxidation of n-Butane," *Applied Catalysis*, 28(1986), pp. 223–233 describes the effect of the process of preparation on the activity of Zr-promoted VPO catalysts. Catalysts prepared by a number of different methods were broken up into 10–20 mesh size and tested for activity. At a P/V of 1.1, the preferred preparation method was simultaneous addition of $H_3PO_4$ and $ZrOCl_2$ to a preformed VPO precursor. Ai reports that the activity per unit surface area was found to pass through a maximum at a Zr/V ratio of about 0.10, while selectivity showed a broad maximum at 0.05 to 0.15.

Tamaki et al., "Promotion of V-P Oxide Catalyst for Butane Oxidation by Metal Additives," Chemistry Letters 1992, The Chemical Society of Japan, pp. 13–16 describes the preparation of VPO catalysts promoted with Bi, Mg, Mn or La. Laboratory reactor results indicated that the addition of a relatively small amount of Bi (Bi/V=0.02) was most effective. VPO catalysts were prepared by mixing $V_2O_5$ powder with benzyl alcohol and isobutyl alcohol, refluxing, adding $H_3PO_4$, and again refluxing to precipitate the precursor. The precursor was calcined to transform it to the active catalyst. Promoted catalysts were prepared by adding an acetylacetonate of Bi, Mg, Mn or La chloride to the organic vanadium solution immediately after the addition of $H_3PO_4$, while the other procedures were the same as for the unpromoted catalyst. The physical form of the catalyst is not disclosed, but a specific surface area of 43 $m^2$/g is reported for the Bi/V=0.02 catalyst. The reference does not disclose when or how the surface area was measured.

U.S. Pat. No. 3,478,063 describes a process for the production of maleic anhydride using an alkene feedstock with a catalyst containing a vanadium-phosphorus oxide with additional elements of nickel and titanium present as the oxides (or phosphates). Butene is the preferred feedstock.

U.S. Pat. No. 3,862,146 discloses a process for the preparation of maleic anhydride that uses a catalyst consisting of vanadium, phosphorus, oxygen, and a metal activator which includes bismuth. All metals are introduced into an aqueous hydrochloric acid solution as chloride salts. Molar yields of maleic anhydride obtained from the promoted catalysts reportedly range from 30 to 51%. This patent teaches promoter/vanadium ratios of at least 0.05 give the best results. A molar yield of 37% maleic anhydride is reported for a catalyst having the atomic ratios of 1.15/1.00/0.19 for P/V/Bi.

U.S. Pat. No. 3,864,280 discloses vanadium-phosphorus oxide catalysts having an intrinsic surface area of from about 7 to about 50 square meters per gram. The catalysts are prepared by precipitation of the vanadium-phosphorus-oxygen complex from an essentially organic solvent medium in the absence of gross amounts of water. The resulting crystalline precipitate is activated by heating in air followed by a 1.5 mole percent butane-in-air mixture, both at elevated temperatures.

U.S. Pat. No. 3,888,886 describes a process for the oxidation of alkanes to dicarboxylic acid anhydrides which uses a vanadium-phosphorus oxide catalyst promoted with certain transition metals that include lanthanum and cerium. All catalyst were prepared from aqueous hydrochloric acid solutions. For 2% butane in air gas streams, operating temperatures with promoted catalysts were no lower than 415° C. with a bed temperature of 450° C. for a Ce/V=0.013 catalyst.

U.S. Pat. Nos. 3,905,914; 3,931,046; and 3,932,305 disclose catalysts made from aqueous solutions containing vanadium-phosphorus oxides and promoted with various zirconium salts. The catalysts were evaluated in fluid bed reactors. In a typical example, a 3.8% butane-in-air gas stream was passed over a fluid bed of catalyst at 425° C. to give a maleic anhydride yield of 41%. An approximate productivity of 44 g maleic anhydride per kg of catalyst per hour is reported for the catalysts of these patents.

U.S. Pat. No. 3,980,585 and 4,049,574 describe improved vanadium-phosphorus oxide catalysts for the conversion of $C_4$ hydrocarbons to maleic anhydride that contain metals from the group Zr, Ce, Zn, La, Hf, U, Sn, alkali, and alkaline earths. Promoters were added to aqueous solutions which were evaporated to yield the solid product. The catalysts of this invention produce maleic anhydride from n-butane with reported molar yields of 25.5 to 57.4% at reactor temperatures of 399° to 450° C.

U.S. Pat. No. 4,020,174 discloses a process for the preparation of maleic anhydride that uses a catalyst composed of vanadium-phosphorus oxide with a metal promoter from a group that includes bismuth. The catalysts of this invention are reactivated by vapor phase treatment with halogen-containing compounds. Molar yields of maleic anhydride using these catalysts are disclosed to range from 43.1 to 52.4% at 400° C. with 1.1% n-butane.

U.S. Pat. No. 4,043,943 describes vanadium-phosphorus oxides isolated from organic solutions which may contain minor amounts of metal promoters selected from groups 4–6 and 15 including the elements Ti, Zr, Hf, Sb, and Bi. The metals are added at the 0.05 to 0.10 level as the oxides and increase the surface areas of the catalysts after equilibration in a butane-oxygen gas stream.

U.S. Pat. Nos. 4,056,487 and 4,105,586 disclose catalyst compositions for the partial oxidation of $C_4$ to $C_{10}$ hydrocarbons to anhydrides comprised of vanadium-phosphorus oxide and a modifier element. Molar yields to maleic anhydride range from 39 to 47% with the catalysts of this invention. Salt bath temperatures for these catalysts range from 394° to 412° C.

U.S. Pat. No. 4,065,468 describes a process for the production of maleic anhydride from n-butane using a catalyst that contains the oxides of vanadium, phosphorus, molybdenum, antimony, and optionally, various promoter elements such as nickel, bismuth, and titanium. For a fixed bed reactor operating at 450° C. a maleic anhydride yield of 20% was observed for a 1 second contact time with a 1.25 butane/air ratioed mixture.

U.S. Pat. No. 4,092,332 discloses a process for preparing maleic anhydride from butane from a titanium and/or silicon promoted vanadium-phosphorus oxide catalyst prepared from aqueous solutions. The catalysts reportedly produce yields of up to 31% maleic anhydride for 3.5% butane-in-air at space velocities around 2500/hr.

U.S. Pat. No. 4,108,874 describes an improved method for making maleic anhydride from vanadium-phosphorus oxides that are promoted with elements that include alkaline earths. The reference describes passing unsaturated four carbon feedstocks over the catalysts at 400° C. to give maleic anhydride in about 60% yields.

U.S. Pat. No. 4,110,350 gives a process for oxidizing unsaturated hydrocarbons having 4 to 6 carbon atoms to maleic anhydride using a catalyst comprised of vanadium-phosphorus oxides and titanium with optionally other elements including titanium, calcium, and zirconium. The aqueous-prepared catalysts are said to produce yields of around 66% to maleic anhydride from 1,3-butadiene at 100% conversion and 450° C.

U.S. Pat. No. 4,132,670 discloses a process for preparing a crystalline vanadium (IV) phosphate catalyst composition having a surface area in excess of 10 square meters per gram. In this process, orthophosphoric acid is reacted with a vanadium (IV) oxycompound by contacting a suspension of the vanadium compound in a hydroxylic organic medium, for example, isobutyl alcohol, with the phosphoric acid at a temperature in the range of 20° C. and 210° C. until the conversion is completed. The resulting catalyst is activated by heating at elevated temperatures in a butane-in-air mixture.

U.S. Pat. No. 4,147,661 discloses a catalyst for the production of maleic anhydride that comprises a vanadium-phosphorus oxide composition with at least one promoter selected from a group that includes antimony with an Sb/V ratio ranging from 0.025 to 1.0. Catalyst surface areas range from 10 to 25 $m^2/g$. Molar yields of maleic anhydride from 50 to 66% are said to be obtained from 1.5% n-butane at gas hourly space velocities of less than 1000/hr.

U.S. Pat. Nos. 4,151,116 and 4,244,878 describe catalysts and a process derived from them that contain vanadium-phosphorus oxide and a post-deposited promoter selected from elements that include lanthanum, cerium, tin, bismuth, and antimony. The catalysts may also include an integrally-incorporated promoter such as titanium. All catalysts and their promoters are made in aqueous hydrochloric acid. Reported molar yields of maleic anhydride for the catalysts of this invention range from 32.0 to 48.8% with selectivities of 40.0 to 61.0% and salt bath temperatures of 410° to 500° C.

U.S. Pat. Nos. 4,152,338 and 4,152,339 disclose catalyst complexes of vanadium-phosphorus oxide with one or more promoter elements prepared from aqueous hydrochloric acid solution to which various amounts of oxalic acid and isopropyl alcohol are added. Catalysts of this invention are said to produce molar yields of maleic anhydride from n-butane from 28.0 to 57.4% with salt bath temperatures from 403° to 450° C.

U.S. Pat. Nos. 4,153,577; 4,158,671; 4,167,516; and 4,202,826 describe vanadium-phosphorus oxide catalysts and processes derived from them that contain modifying elements that include Ce with a Ce/V ratio from 0.0054 to 0.20. Catalysts are prepared in aqueous hydrochloric acid solutions in which the promoter salts are dissolved in HCl. Catalysts of this invention operate with n-butane concentrations of 1.4 to 1.6%, reportedly giving molar yields of maleic anhydride of from 40.1 to 48.0% at salt bath temperatures from 388° to 410° C.

U.S. Pat. Nos. 4,172,084; 4,218,382; 4,219,484; and 4,225,465 describe catalysts of vanadium and phosphorus from aqueous oxide slurries that include promoter elements of cerium, antimony, bismuth, and lanthanum. Molar yields of maleic anhydride of up to 54.9% are reported.

In U.S. Pat. No. 4,187,235, a process is described for preparing maleic anhydride from n-butane in the presence of a vanadium-phosphorus oxygen high surface area catalyst, that is, 10 to 100 square meters per gram (BET method). The catalyst is prepared by reducing pentavalent vanadium to a valence between +4.0 and +4.6 with a substantially anhydrous primary or secondary alcohol and contacting the reduced vanadium with phosphoric acid, followed by recovering and calcining the resulting vanadium (IV) phosphate compound.

U.S. Pat. Nos. 4,209,423; 4,222,945; 4,288,372; and 4,317,777 disclose catalysts and processes derived from them for the oxidation of hydrocarbons to acid anhydrides. The catalysts are prepared from hydrohalic acid solutions from which catalyst precursors were obtained. The catalyst precursors are extracted with boiling water, dried, pelleted, and sieved to particles that are impregnated with various promoters, particularly the rare earth elements of lanthanum and cerium. Catalysts of these inventions are said to have surface areas of 10 to 20 m$^2$/g and produce maleic anhydride from 1.5% n-butane (400 to 1000/hr. GHSV) in molar yields of from 49 to 60% at temperatures from 385° to 450° C.

U.S. Pat. Nos. 4,251,390 and 4,283,307 give improved oxidation catalysts for the oxidation of butane to maleic anhydride containing the promoter elements of Zn, Si, La, Ge, Sn, Ti, Zr, Sb, Bi, Ni, Ce, Hf, U, alkali, and alkaline earths. Catalysts of this invention are described as producing about 60 g maleic anhydride per kg catalyst per hour while operating at around 400° C. with 0.9% butane-in-air at a space velocity of 2500/hr.

U.S. Pat. Nos. 4,292,201 describes a method for preparation of a hydrocarbon oxidation catalyst that includes a vanadium-phosphorus oxide catalyst composition to which a promoter such as cerium is added. The active phase is identified as VO(PO$_3$)$_2$ and is prepared in an aqueous phase with the Ce promoter to yield a catalyst having a surface area after calcination at 500° C. of about 4 m$^2$/g. Unsaturated hydrocarbons such as 1-butene are fed to the catalyst at high conversions with a reported 63 to 67% selectivity to maleic anhydride.

U.S. Pat. No. 4,328,120 discloses a vanadium-phosphorus oxide catalyst prepared from isobutanol with HCl and with a uranium promoter. Molar yields of about 50% to maleic anhydride were observed with a 1.05% butane-in-air gas feed.

U.S. Pat. No. 4,337,173 gives processes for preparing vanadium-phosphorus oxide catalysts that include the promoter elements of Fe, Cr, and Al. The precursor oxide is prepared from aqueous solutions. Yields of 70% maleic anhydride from 1.5% butane are disclosed for operation at a space velocity of 500/hr.

U.S. Pat. Nos. 4,351,773 and 4,525,471 describe fluid bed butane oxidation catalysts prepared from a mixture of vanadium-phosphorus oxides and promoted optionally with U, Zn, Hf, Zr, Sb, Bi, Sn, Ce, and rare earths. The use of these and other promoters for butane oxidation is described but not differentiated in enhanced yield, stability, operating conditions, or physical properties from the unpromoted catalyst.

U.S. Pat. Nos. 4,371,702; 4,442,226; 4,632,916; and 4,699,985 describe vanadium-phosphorus oxide catalysts and processes derived from them for vapor phase oxidation of n-butane to maleic anhydride containing nonpost-deposited promoters that include antimony and mixtures of antimony with indium, tantalum, and silica. Catalysts are prepared from a mixture of isopropyl alcohol and benzyl alcohol containing V$_2$O$_5$. Portions of Si(OEt)$_4$ and alkoxides of Ta and Sb dissolved in ethanol are added at intervals during reflux, then H$_3$PO$_4$ is added to precipitate a solid which is further refluxed for a period of time before isolation by filtration. Vacuum-dried solids are pelleted with a binder and activated in air at 380° to 400° C. and then in 1.5% n-butane and air at temperatures up to 485° C. After cooling in this gas stream the catalyst was operated at 425° C. to produce maleic anhydride. The 10-to-20 mesh catalyst recovered from this treatment reportedly had a BET surface area of 28.0 m$^2$/g and an average vanadium valence of +4.0. Molar yields of maleic anhydride obtained with these catalysts were described as ranging from 51 to 69%.

U.S. Pat. Nos. 4,396,535 and 4,465,846 disclose improved vanadium-phosphorus oxide catalysts and processes derived from them for the production of maleic anhydride. The catalysts are prepared from reflux of α-VOPO$_4$ in a reducing organic solution. Various promoter elements that include Sb, Bi, Sn, and the lanthanides are incorporated into the catalyst prior to reduction of the vanadium. At 85% n-butane conversion, catalysts of this invention are said to produce molar yields of maleic anhydride from 54.8 to 56.1%.

U.S. Pat. Nos. 4,400,522 and 4,448,893 describe vanadium-phosphorus oxide catalysts prepared from isobutanol with the addition of various promoter elements including U, Zn, Hf, and Zr. The catalysts are useful for C$_4$ oxidations with air.

U.S. Pat. No. 4,456,764 discloses a process for preparing maleic anhydride through the use of a catalyst prepared from vanadium-phosphorus oxides and promoted with elements that include titanium and cerium. The promoted catalysts are prepared by hydrothermal crystallization and show improved yields of maleic anhydride over the unpromoted catalyst.

U.S. Pat. Nos. 4,560,674; 4,562,268; and 4,567,158 describe a class of high productivity catalysts for the vapor phase synthesis of maleic anhydride from butane with air. The catalysts are prepared from isobutyl alcohol and reportedly exhibit higher productivities under comparable operating conditions than catalysts prepared by other means. Zinc is illustrated as a promoter element.

U.S. Pat. Nos. 4,604,371; 4,639,530; 4,782,166; and 4,801,567 disclose C$_4$ to C$_{10}$ hydrocarbon oxidation catalysts consisting of vanadium-phosphorus oxide active phases with a promoter element such as tin. All catalysts are prepared in combination with a zeolite (SiO$_2$/Al$_2$O$_3$ ratio of at least 6.0) carrier. The catalysts produce maleic anhydride from n-butane but examples indicate temperatures of about 500° C. are required to give practical yields.

U.S. Pat. No. 4,649,205 discloses a process for the reactivation of a vanadium-phosphorus oxide catalyst promoted by metals from a group that includes tin. The catalysts of this invention benefit by the use of water/-trialkylphosphate mixtures fed to the reactor with n-butane/air. Molar yields of 47.9 to 54.4% maleic anhydride are disclosed for these catalysts with per day productivities ranging from 0.79 to 1.76 lb.-maleic anhydride/lb.-catalyst.

U.S. Pat. No. 4,732,885 describes a process for the manufacture of vanadium-phosphorus oxide (VPO)

catalysts using a cometal as a promoter from a group that includes tin and molybdenum. The cometal/vanadium ratio may range from 0.001 to 0.4. The promoted catalysts are used in the production of maleic anhydride from n-butane. The catalyst is prepared from an organic ether solvent containing a phosphoryl chloride in the presence of water or an aliphatic alcohol. The catalyst is activated in a gas stream of n-butane and water. An Sn-promoted VPO catalyst having Sn/V=0.03 reportedly displayed a yield of 47.9% maleic anhydride when a 1.1% n-butane gas stream was passed over the catalyst at 405° C. and 1200/hr. space velocity.

U.S. Pat. No. 4,748,140 describes a process for activating a fluid bed vanadium-phosphorus oxide catalyst for the production of maleic anhydride from n-butane. The catalysts of this invention contain promoter elements selected from a group that includes cerium and rare earths.

U.S. Pat. No. 4,784,981 discloses vanadium-phosphorus oxide catalysts that are promoted with elements which include Zn and Ni in preferred M/V ratios of 0.02 to 0.07. The mixed oxide catalysts are prepared from alcohol solutions. The catalysts are used for converting $C_4$ hydrocarbons to maleic anhydride at 410° to 450° C.

U.S. Pat. No. 4,801,569 describes novel vanadium-phosphorus oxide (VPO) catalysts for the preparation of maleic anhydride by catalytic oxidation of a hydrocarbon such as n-butane. Promoter elements that include nontransition metal oxides of La, Sb, Sn, and Bi supported at the 20 wt.-% level on a silica carrier are physically blended with active VPO to give catalysts of this invention. The resulting catalytic material typically contains 90 wt.-% VPO and 10 wt.-% promoter/silica. The catalysts of this invention offer improved catalyst lifetime and resistance to thermal shock. Molar yields of 42.5% maleic anhydride are represented for the promoted catalyst compositions of this invention compared to 41.5% yield for unpromoted compositions.

U.S. Pat. No. 4,824,819 discloses catalysts for the production of maleic anhydride which are comprised of vanadium-phosphorus oxide and a cometal selected from a group with bismuth, tin, and antimony. A vanadium compound is deposited on top of the VPO/cometal composition to give the final catalyst. Catalysts of this invention are described as exhibiting 89% conversion of a 1.1% n-butane/air feed at 1200/hr. space velocity at 403° C. with 61.5% molar yield of maleic anhydride.

U.S. Pat. No. 4,950,769 describes a process for vapor phase oxidation of n-butane to maleic anhydride by a vanadium-phosphorus oxide catalyst containing a cometal selected from a group that includes tin. A peroxide is added to the reactor gas stream to improve the catalyst operation.

U.S. Pat. Nos. 4,957,894, 4,965,235, 5,093,298, and 5,095,125 disclose processes for the manufacture of catalysts used for maleic anhydride production. The catalysts are comprised of vanadium-phosphorus oxide and contain a cometal as a promoter from a group that includes tin, bismuth, and antimony. Catalysts prepared by processes of this invention do not exhibit more than 2% expansion when activated for the oxidation of n-butane to make maleic anhydride.

U.S. Pat. No. 4,996,179 describes catalysts for the production of maleic anhydride by oxidation of n-butane and composed of vanadium-phosphorus oxide along with a cometal promoter selected from a group that includes bismuth, antimony, and tin. The catalysts are formed into various geometric shapes and are treated in an inert atmosphere between 343° and 704° C. The catalysts of this invention reportedly produce molar yields of maleic anhydride around 53% for a 1.1% n-butane stream passing over the catalyst at 1200/hr. space velocity.

Thus, it has long been known that various promoters, including Bi, Zr, Sn, etc. can be added to VPO catalysts to obtain improved performance. For example, numerous patents from the mid-1970s (for example, Jurewicz et al. U.S. Pat. No. 3,905,914, Weinstein et al. U.S. Pat. No. 3,931,046, and Jurewicz et al. U.S. Pat. No. 3,932,305, all assigned to Mobil Oil Corp.) disclose the benefit of Zr addition in preparing aqueous derived catalysts. Since then, VPO catalysts prepared in aqueous media have been outpaced by catalysts prepared in non-aqueous media. See the Hutchings article discussed above. As indicated by the Ai article cited above, zirconium has been suggested for VPO catalysts prepared in non-aqueous systems, in optimal Zr/V ratios of about 0.10 in catalysts of 10-20 mesh. Tamaki suggests a Bi/V ratio of 0.02 for a catalyst prepared in a nonaqueous system, but does not mention catalyst particle size or refer to the preparation of the tablets or pellets typically used in commercial fixed bed reactors for the manufacture of maleic anhydride.

Conventionally, a VPO catalyst is fully activated only after several hundred hours of operation in which a stream containing air or oxygen and a hydrocarbon such as n-butane is passed over the catalyst and the hydrocarbon contained in the stream is oxidized to maleic anhydride in the presence of the catalyst at temperatures in excess of 300° C. Commonly, a phosphorus compound is included in the gas stream for the purpose of maintaining the activity of the catalyst. While the function of the phosphorus compound is not fully understood, it is generally believed to counter the deleterious effects of excessive phosphorus depletion of the catalyst under high temperature catalytic reaction conditions.

Laboratory reactors used for catalyst evaluation are typically charged with relatively fine particle catalysts comprising VPO grains of roughly 1 to 2 mm in size. It has been discovered that, when such fine grain catalysts are conditioned by exposure to n-butane oxidation in a laboratory reactor, the B.E.T. surface area increases over the course of a few hundred hours operation by something in the range of about 15–25%, or more. For example, it has been found that a catalyst initially exhibiting a B.E.T. surface area of 28 $m^2/g$ will typically exhibit an area of about 35 $m^2/g$ after 200–400 hours exposure to n-butane oxidation. The B.E.T. surface area developed after exposure to reaction between air or oxygen and n-butane or another hydrocarbon is referred to as the "developed surface area" of the catalyst. Fine grain catalysts having developed surface areas in the range of 35 $m^2/g$ are generally very active.

However, pressure drop considerations preclude the use of fine catalysts in commercial fixed bed reactors. Catalysts that are coarse enough for commercial fixed beds typically have dimensions of at least about an eighth of an inch (about 3.2 mm), and are preferably in the range of 5/32" (about 4 mm) to ½" (about 13 mm). To prepare such catalysts, granular VPO precursor compositions are conventionally tabletted into shaped bodies, and the shaped bodies are subjected to calcination to convert the VPO to the active catalyst form, i.e., a form that contains a substantial fraction of $(VO)_2P_2O_7$. The so-activated tablet or pellet is then placed in a reactor and exposed to the oxidation of butane or another hydrocarbon for several hundred hours to develop the full activity of the catalyst. In commercial operation of a fixed bed VPO reactor, it is also an advantageous practice to inject a phosphorus compound into the hydrocarbon/air stream to maintain catalyst activity, and it has previously been considered desirable to begin injection of a phosphorus compound, such as trimethyl phosphate or trimethyl phosphite, at or shortly after the initial introduction of the hydrocarbon/air stream in the conditioning of the catalyst.

Experience has shown that, unlike the fine grain catalyst that is typically used in laboratory reactors, the shaped bodies used for commercial fixed bed reactors do not consistently exhibit an increase in surface area upon conditioning by exposure to the reaction of hydrocarbon and oxygen. Moreover, shaped catalyst bodies such as spheres, rings, and the like do not ordinarily have as great a specific surface area initially as do fine grain catalysts. For example, if produced by precipitation from an organic medium, a typical shaped body VPO catalyst exhibits a B.E.T. surface area of 10 to 20 $m^2/g$ after activation. If the catalyst does not contain a promoter, the developed surface area may or may not be higher than the activated surface before conditioning, but in any case the developed surface is seldom greater than about 22-23 $m^2/g$. Generally, the activity per unit weight of a VPO catalyst is a direct function of the effective specific surface area of the catalyst. Thus, the shaped body catalysts, which are necessary in commercial fixed bed reactors to provide acceptable pressure drop characteristics, have not usually exhibited the same high activity per unit weight that may be demonstrated for the same catalyst in fine grain form in a laboratory reactor.

Published literature reports very high surface areas for VPO catalysts that contain or are supported on silica or zeolite. However, in these instances, much of the measured surface area is essentially inactive and the normal direct relationship between surface area and activity per unit weight does not prevail. Consequently, the catalysts utilizing silica or zeolite have not fulfilled the need in the art for a shaped body VPO catalyst of enhanced active surface area.

SUMMARY OF THE INVENTION

Accordingly, among the several objects of the invention are the provision of a vanadium phosphorus oxide catalyst of improved activity, selectivity and productivity; the provision of such a catalyst in a shaped body form suitable for use in a commercial fixed bed reactor for the preparation of maleic anhydride; the provision of such a shaped body catalyst having an enhanced developed surface area; the provision of such a catalyst which may optionally be produced without the need for corrosive reducing agents and solvents; the provision of improved methods for producing VPO catalyst precursors and activated VPO catalyst, especially in shaped body form suitable for use in a commercial fixed bed reactor; and the provision of such a method which optionally does not utilize corrosive reducing agents or solvents.

Briefly, therefore, the present invention is directed to an active phosphorus vanadium oxide catalyst for the conversion to maleic anhydride of a non-aromatic hydrocarbon having at least four carbon atoms in a straight chain. The catalyst comprises a shaped body having a volume of at least about 0.02 cc. It has been equilibrated to provide a developed surface area of at least about 28 $m^2/g$ and contains a promoter selected from among bismuth, antimony, germanium, titanium, zirconium, lanthanum, cerium, uranium, nickel, zinc, tin, silicon, and mixtures thereof. The promoter is present in such a proportion as to enable the catalyst to have the aforesaid developed surface area and to exhibit a weight/area productivity of at least about 3.5 mg maleic anhydride per $m^2$ hour and/or a weight/weight productivity of at least about 100 g maleic anhydride kg- catalyst hour when contacted with a gas containing 2.4% by volume n-butane in air at a gas flow volume to catalyst weight ratio of 2180 cc/g-min. under a pressure of $1.055 \times 10^2$ kPa-G, and at a temperature sufficient to maintain a hydrocarbon conversion of 85 mole percent. The catalyst may also comprise a fixed bed of shaped bodies having an average volume of at least about 0.02 cc and containing the promoter, having the surface area, and exhibiting the productivities described above.

The invention is further directed to an active phosphorus vanadium oxide catalyst containing a promoter selected from among bismuth, antimony, germanium, titanium, zirconium, lanthanum, cerium, uranium, zinc, nickel, tin, silicon, and mixtures thereof. The catalyst corresponds to the formula:

$$(VO)_2(M)_mP_2O_7.b(P_2/_cO)$$

wherein M comprises bismuth, antimony, germanium, titanium, zirconium, lanthanum, cerium, uranium, zinc, nickel, tin, silicon, or mixtures thereof, m is a number from about 0.005 to about 0.04, b is a number taken to provide a P/V atom ratio of from about 0.95 to about 1.3, and c is a number representing the oxidation number of phosphorus and has a value of 5. The catalyst has a crystal structure corresponding to that of a catalyst that has been activated by a process comprising the following steps. A catalyst precursor composition is heated in an atmosphere selected from the group consisting of air, steam, inert gas, and mixtures thereof, to a temperature not to exceed 300° C. The precursor composition corresponds to the formula:

$$VO(M)_mHPO_4.aH_2O.b(P_2/_cO).n(organics)$$

wherein M, m, b, and c are as defined above, a is a number of at least about 0.5, and n is a number taken to represent the weight percent of intercalated organics component. The catalyst precursor is maintained at the temperature of the previous step and an atmosphere is provided containing molecular oxygen, steam, and optionally an inert gas. The atmosphere is represented by the formula:

$$(O_2)_x(H_2O)_y(IG)_z$$

wherein IG is an inert gas and x, y, and z represent mole percent of the $O_2$, $H_2O$, and IG components, respectively, in the molecular oxygen/steam-containing atmosphere, with x having a value greater than zero (0 mole percent) but less than 100 mole percent, y having a value greater than 0 mole percent but less than 100 mole percent, and z having a value representing the balance of the molecular oxygen/steam-containing atmosphere. The temperature is increased at a programmed rate of from about 2° C. per minute to about 12° C. per minute to eliminate the water of hydration from the catalyst precursor. The temperature from the previous step is adjusted to a value greater than 350° C. but less than 550° C. and the adjusted temperature is maintained in the molecular oxygen/steam-containing atmosphere for a time effective to provide a vanadium oxidation state of from about +4.0 to about +4.5. The adjusted temperature is continually maintained in a non-oxidizing steam-containing atmosphere for a time effective to complete the catalyst precursor to active catalyst transformation to yield the active catalyst. The invention is also directed to the aforesaid process for transformation of the precursor to the active catalyst.

The invention includes a further process for the preparation of a catalyst represented by the formula:

$$(VO)_2(M)_mP_2O_7 \cdot b(P_2/_cO)$$

wherein M, m, b, and c are as defined above. In this process, a slurry is prepared comprising a substantially pentavalent vanadium-containing compound and a pentavalent phosphorus-containing compound in an alcohol medium capable of reducing the vanadium to a valence state less than +5, and an alcohol modifying agent effective, upon reaction of the vanadium compound and the phosphorus compound, to promote the formation of a precipitate having a macrostructure predominantly consisting of radially oriented three-dimensional networks of randomly shaped open cells. A compound comprising M is introduced into the slurry and the slurry is heated for a time sufficient to precipitate a catalyst precursor composition containing M. The precipitated precursor composition is separated from the supernatant liquid phase and dried. The dried precursor composition is formed into shaped bodies and calcined to transform it into an activated catalyst.

The invention is further directed to another process for the preparation of catalyst represented by the formula:

$$(VO)_2(M)_mP_2O_7 \cdot b(P_2/_cO)$$

wherein M, m, b, and c are as defined above. In this process, a pentavalent vanadium-containing compound is reacted with a pentavalent phosphorus-containing compound in an alcohol medium containing a stoichiometric excess of phosphorus compound with respect to vanadium compound, the reaction being carried out until the vanadium compound is substantially exhausted by reaction with the phosphorus compound. A compound comprising M is introduced into the slurry and the slurry containing the compound comprising M is heated to cause formation of a solid phase phosphorus vanadium oxide catalyst precursor composition containing M. The solid phase precursor composition is separated from the supernatant liquid phase and dried. The dried precursor composition is formed into shaped bodies and processed to transform it into an active catalyst.

The invention is directed to still another process for the preparation of catalysts represented by the formula:

$$(VO)_2(M)_mP_2O_7 \cdot b(P_2/_cO)$$

wherein M, m, b, and c are as defined above. In this process, a slurry is prepared comprising a substantially pentavalent vanadium-containing compound and a pentavalent phosphorus-containing compound in an alcohol medium capable of reducing the vanadium to a valence state of less than +5. A compound comprising M is introduced into the slurry and the slurry is heated for a time sufficient to precipitate a catalyst precursor composition containing M. The precipitated precursor composition is separated from the supernatant liquid phase and dried. The dried precursor composition is formed into shaped bodies and processed to transform it to an activated catalyst. The activated catalyst is contacted with a stream of reactant gases comprising oxygen and a non-aromatic hydrocarbon having at least four carbon atoms in a straight chain, the stream being substantially free of any phosphorus compound. The hydrocarbon is reacted with oxygen in the presence of the catalyst. The catalyst is contacted with the stream and the reaction carried out in the presence of the catalyst for a period of time sufficient to bring the B.E.T. surface area of the catalyst to equilibrium.

Other objects and features will be in part apparent and in part pointed out hereinafter.

DESCRIPTION OF THE PREFERRED EMBODIMENTS

In accordance with this invention, it has been discovered that vanadium phosphorus oxide catalysts of enhanced specific surface area, and consequently enhanced activity for the oxidation of $C_4$ hydrocarbons to maleic anhydride, may be produced by incorporating into the catalyst certain selected promoters in carefully controlled amounts. In particular, it has been found that certain relatively small and controlled proportions of bismuth, antimony, germanium, titanium, zirconium, lanthanum, cerium, uranium, nickel, zinc, tin, silicon, and mixtures thereof are effective to allow the B.E.T. developed surface area of a shaped body vanadium phosphorus oxide catalyst, or the average developed B.E.T. surface area of a fixed bed of such shaped catalyst bodies, to be greater than 28 m$^2$/g. Developed surface areas of this magnitude are achieved by contacting the shaped bodies comprising the promoted VPO catalyst with a stream of reactant gases comprising oxygen and a nonaromatic hydrocarbon having at least four carbon atoms in a straight chain, and reacting the hydrocarbon and oxygen in the presence of the catalyst body, for an appropriate period of time, typically about 150 to about 400 hours.

The point at which the developed surface area of the catalyst reaches a maximum after exposure to the oxygen/hydrocarbon reaction may be considered an equilibrium point, and the process of bringing the developed surface area to its maximum by exposure to this reaction is referred to as "equilibration" of the catalyst. The exposure effective for equilibration is essentially the same as that used for "conditioning" a VPO catalyst in accordance with established practice. It has been discovered that, upon equilibration, the shaped body catalysts of the invention consistently exhibit a developed surface area of at least 28 m$^2$/g.

It has further been found that the developed surface area of the catalyst of the invention is consistently higher than the developed surface of catalysts containing the higher proportions of promoters that are typically called for in the prior art. Such higher proportions are not consistently effective to cause a significant increase in the B.E.T. surface area upon equilibration of a shaped body catalyst. Preferably, it has been found that the promoter element should be present in a proportion of between about 0.005 and about 0.04 moles per mole of vanadium in the catalyst. More preferably, the promoter element is present in a proportion of between about 0.007 and about 0.02 moles per mole vanadium. However, for certain promoters, the preferred ratio is in the lower end of these ranges. For example, it has been found that bismuth is most effective at a Bi/V ratio of between about 0.007 and about 0.015. More generally, the proportion of promoter should be such as to enable the catalyst to have a developed surface area of at least about 28 $m^2/g$. The proportion of promoter should also be sufficient to enable the catalyst to exhibit a weight/area productivity of at least about 3.5 mg maleic anhydride/$m^2$-hr and/or a weight/weight productivity of at least about 100 g maleic anhydride/kg.cat.-hr. when contacted with a gas containing 2.4% by volume n-butane in air, at a gas flow volume to catalyst weight ratio of 2180 cc/g-min. under a pressure of $1.055 \times 10^2$-kPa-G, and at a temperature sufficient to maintain a hydrocarbon conversion of 85 mole percent.

For the most advantageous performance properties, it is further preferred that the total proportion of all promoter elements, including those required for the invention and any others that may be present, not exceed about 0.04 moles per mole vanadium. Those skilled in the art will understand what other elements may be considered promoter elements for VPO catalysts. Most of the metallic and semiconductor elements have some effect, or have been proposed, as promoters for VPO catalysts used for the oxidation of $C_4$ hydrocarbons to maleic anhydride. These include, for example, Li, Na, Mg, Al, Ti, Cr, Mn, Fe, Co, Cu, Ca, Y, Nb, Mo, Ru, Ag, Sn, Ba, La, the rare earth metals, Hf, Ta, W, Re, and Th. Preferably, material proportions of promoter elements other than Bi, Sb, Ge, Ti, Zr, U, La, Ce, Ni, Zn, Sn, Si, and mixtures thereof are excluded from the catalyst. However, minor functional proportions of other promoter elements may be tolerated, provided that the ratio of the sum of the molar proportions of all promoter elements to the proportion of vanadium in the catalyst does not exceed about 0.04.

For conversion of n-butane to maleic anhydride by reaction of a mixture of n-butane and air, bismuth and zirconium are particularly preferred promoters. However, nickel, zinc, cerium, lanthanum, and tin have also been demonstrated to provide superior performance in this embodiment of the invention. To similar effect are promoter elements selected from the group consisting of antimony, germanium, titanium, uranium, and silicon. Accordingly, demonstrably active promoter elements may be selected from among bismuth, antimony, germanium, titanium, zirconium, lanthanum, cerium, uranium, zinc, nickel, tin, silicon, and mixtures thereof.

Shaped bodies having pressure drop characteristics acceptable for commercial fixed bed reactors typically have a principal dimension of at least about ⅛", more typically 5/32" to ¼". Generally, therefore, the catalyst has a volume per body of at least about 0.02 cc, more commonly at least about 0.03 cc, and most preferably at least about 0.05 cc. In the range above about 0.02 cc, the presence of the proper amount of promoter has a critical effect on the susceptibility of the catalyst to development of an enhanced surface area upon equilibration.

The promoted catalysts of the invention are useful for the partial oxidation of nonaromatic hydrocarbons having at least four carbon atoms in a straight chain with molecular oxygen or a molecular-oxygen containing gas in the vapor phase to maleic anhydride. Preferably, these catalysts are prepared by the general procedures given in U.S. Pat. Nos. 4,562,268 and 4,560,674 which are herein incorporated by reference. The catalysts prepared by these procedures exhibit a highly uniform macrostructure that predominantly comprises generally spheroidal particles of radially oriented three-dimensional networks of randomly shaped open cells. In the processes otherwise fully described in these patents, promoter elements are added at times during the catalyst precursor preparation that preserve the open cell morphology but insure maximum benefit to catalyst performance from the presence of promoter elements. It should be understood, however, that the advantageous effect of the proper amount of a selected promoter is not limited to catalysts of open cell morphology, but is also realized in catalysts of a variety of different forms. See, for example, the various surface textural characteristics illustrated in the figures of U.S. Pat. No. 4,562,268, the macrostructures of which include: striated spherical particles composed of a succession of layers stacked one upon another (FIGS. 7–10 of '268); and clusters of small groups of associated platelets (FIGS. 11 and 12 of '268).

For purposes of this invention, the term "yield" means the ratio of the moles of maleic anhydride obtained to the moles of hydrocarbon feedstock introduced into the reactor multiplied by 100. The term "selectivity" means the ratio of the moles of maleic anhydride obtained to the moles of hydrocarbon feedstock reacted or converted multiplied by 100 with the terms expressed as mole percent. The term "conversion" means the ratio of the moles of hydrocarbon feedstock reacted to the moles of hydrocarbon feedstock introduced into the reactor multiplied by 100 with the term expressed as mole percent. The term "weight/weight productivity" means the weight of maleic anhydride produced per unit weight of catalyst per hour. The term "weight/area productivity" means the weight of maleic anhydride produced per unit B.E.T. developed surface area of catalyst per hour. The term "space velocity" or "gas hourly space velocity" or "GHSV" means the volumetric flow rate of gaseous feed expressed in standard (273K and 14.7 psig) cubic centimeters per hour divided by the bulk catalyst volume expressed in cubic centimeters with the term expressed as cc/cc/hour or simply, $hr^{-1}$. The term "gas flow volume to catalyst weight ratio" means the ratio of the volumetric flow rate of a gas containing a hydrocarbon and air or oxygen to the weight of a catalyst bed through which the gas is flowing, expressed in g/cc-min.

VPO catalysts are prepared by reaction of a vanadium compound and a phosphorus compound to produce a precursor, and activation of the precursor by calcination to convert a substantial fraction of the precursor composition to vanadyl pyrophosphate. For fixed bed catalysts, the precursor is formed into a body of the desired shape before heat treatment to transform the precursor composition to active catalyst. In the synthesis of promoted VPO catalysts, the character of the catalyst obtained is affected by the compatibility of the chemistry of the promoter system with the precursor chemistry, the influence of the promoter on the transformation of the precursor to the active phase, and the effect of the promoter concentration on the development of the active phase and of the specific surface area of the catalyst upon equilibration.

The most preferred routes to VPO catalysts are by way of the precursor compound $VOHPO_4.0.5H_2O$.

There are numerous established synthetic options for the preparation of this precursor, and the procedures yield widely varying macrostructures. Generally the aforesaid precursor can accommodate nonstoichiometry, i.e., a P/V ratio of about 0.95 to about 1.3, intercalated organic material, such as the alcohol of the reaction medium, and promoter elements, with minor structural modifications. The vanadium compounds useful as a source of vanadium in the catalysts of the instant invention in general are those containing pentavalent vanadium and include vanadium pentoxide or vanadium salts, such as ammonium metavanadate, vanadium oxytrihalides, and vanadium alkylcarboxylates. Among these compounds, vanadium pentoxide is preferred.

The phosphorus compounds useful as a source of phosphorus in the catalyst employed in the instant invention are preferably those that contain pentavalent phosphorus. Suitable phosphorus compounds include phosphoric acid, phosphorus pentoxide, or phosphorus perhalides such as phosphorus pentachloride. Of these phosphorus-containing compounds, phosphoric acid and phosphorus pentoxide are preferred.

The catalysts of the instant invention are normally prepared by introducing a substantially pentavalent vanadium-containing compound and a pentavalent phosphorus-containing compound into an alcohol medium capable of reducing in part the vanadium to a valence state of less than +5 to form a slurry.

The resultant slurry is contacted with an effective amount of an alcohol-modifying agent capable of changing the state of the alcohol to a state conducive to the formation of the catalyst precursor. The exact function and mode of action of the alcohol-modifying agent is not completely understood. While not desiring to be bound by theory of the invention or to limit the invention in any way, it is believed that the alcohol-modifying agent alters the surface tension of the alcohol to enhance intimate contact among the phosphorus-containing compound, the vanadium-containing compound, and the alcohol, and thereby promotes the formation of the highly porous catalyst precursor having the open cell morphology which is convertible by a controlled sequence of gas and thermal treatments into the catalyst of the instant invention. Suitable, but nonlimiting, alcohol-modifying agents include hydrogen iodide, sulfur dioxide, fuming sulfuric acid, surfactants as described in U.S. Pat. No. 4,149,992, which specification is herein incorporated by reference, formic acid, oxalic acid, and citric acid. Of these alcohol-modifying agents, oxalic acid is preferred.

The amount of alcohol-modifying agent employed is not narrowly critical. All that is necessary, as previously noted, is that the amount employed be sufficient to modify the alcohol to a state that is conducive for the formation of the catalyst precursor. An amount sufficient to provide an alcohol-modifying agent/vanadium-containing compound mole ratio of 0.64 is normally employed. Larger or smaller amounts may, however, be employed, if desired, for example in the range of between about 0.4 and about 1 moles per mole of vanadium.

The phosphorus-containing compound may be introduced into the vanadium/alcohol/alcohol-modifying agent mixture in any convenient manner. It may be added in the form of a solution or suspension in the alcohol medium or component of the mixture, or when the phosphorus-containing compound is in liquid form, such as >100% phosphoric acid, it may be added alone.

Alternatively, a vanadium-containing compound and a phosphorus-containing compound, such as >100% phosphoric acid may be introduced simultaneously into the alcohol medium. In yet another mode, the vanadium-containing compound is introduced into a solvent or dispersion of the phosphorus-containing compound in the alcohol. It is preferred, however, to introduce the phosphorus-containing compound to a mixture of the alcohol-modifying agent, the vanadium-containing compound, and the alcohol.

The alcohols employed in the preparation of the catalysts of the instant invention are preferably anhydrous and must be capable of reducing at least a portion of the vanadium to a +4 valence state, either upon addition of the vanadium-containing compound or upon mixing and heating. In addition the alcohol should be a solvent for the phosphorus-containing compound especially the preferred phosphoric acid, and relatively unreactive toward the phosphorus-containing compound. Preferably, the alcohol is not a solvent for the catalyst precursor mixed oxides of phosphorus and vanadium. In those instances wherein the catalyst precursor is soluble in the alcohol medium, precipitation should be easily induced by removal of a portion of the alcohol. Suitable alcohols include primary and secondary alcohols, such as methanol, ethanol, 1-propanol, 2-propanol, 1-butanol, 2-methyl-1-propanol (isobutyl alcohol), 2-butanol, 3-methyl-2-butanol, 2,2-dimethyl-1-propanol, 4-methyl-2-pentanol, and 1,2-ethanediol (ethylene glycol). Of these alcohols, isobutyl alcohol (IBA) is preferred.

After the phosphorus and vanadium compounds are introduced into the alcohol medium to form the alcohol/alcohol-modifying agent/vanadium-containing compound/phosphorus-containing compound mixture, reduction of at least a portion of the vanadium to a valence state of +4 is effected, preferably by heating the mixture, with stirring, if desired, until a blue solution or slurry is obtained. In general, heating the mixture at reflux temperature for a period of time ranging from about four hours to 20 hours is sufficient.

The promoter elements may be added as solids, suspension of solids, or solutions to the catalyst precursor slurry. Promoter compounds that may serve as sources of the promoter elements include metal halides, metal alkoxides, and metal carboxylates. Of these compounds, metal carboxylates are preferred. Suitable carboxylates for metal salts include formate, acetate, propionate, butyrate, isobutyrate, pentanoate, hexanoate, heptanoate, octanoate, nonanoate, decanoate, and 2-ethylhexanoate. Of these carboxylates, 2-ethylhexanoate is preferred.

The promoter elements can be added as metal 2-ethylhexanoates in solutions of alcohols, esters, aromatics, and alkanes. Of these solvents, isobutyl alcohol, isobutyl isobutyrate, decane, and mineral spirits constitute preferred but not limiting solvents of choice. Typically, the metal 2-ethylhexanoates are dissolved in suitable solvents in amounts of 20 percent by weight or less.

The promoter metal 2-ethylhexanoates may be added to the vanadium-phosphorus oxide catalyst precursor slurry before, during, or after the reflux period at slurry temperatures ranging from ambient to the reflux temperature of the catalyst slurry mixture. Of these times of addition, during the reflux period is preferred and at a slurry temperature of less than 40° C. Because the promoter source is generally reactive with the phosphorus compound, it is preferably withheld from the reaction system until the vanadium compound has been substantially consumed by reaction to a VPO compound. Otherwise, it may be necessary to increase the P/V ratio above the optimum for the purpose of driving the reaction of the vanadium compound to completion. A preferred method of preparation, therefore, is referred to as the "post" method, in which the vanadium compound is first reacted at elevated temperature with a modest excess of phosphorus compound, for example, at a P/V ratio of 1.05 to 1.20, until the vanadium compound is substantially exhausted; and thereafter the promoter source compound is reacted with the residual phosphorus compound to incorporate the promoter in the catalyst precursor composition. The reaction between the vanadium and phosphorus compounds is carried out a temperature in the range of between about 90° and about 120° C., conveniently at atmospheric reflux temperature. The reaction mixture is then cooled to below 40° C. for addition of the promoter source.

In a more preferred method, the vanadium compound and phosphorus compound are reacted at a temperature in the range of between about 90° C. and about 120° C., again using a P/V ratio of 1.05 to 1.15; the reaction mixture is cooled below 40° C. for addition of the promoter source, and optionally a further increment of phosphoric acid; and then the reaction system is again heated to a temperature in the range of between about 90° C. and about 120° C. for incorporation of the promoter compound into the precursor structure. Because both the V-P reaction and the incorporation of the promoter are advantageously conducted at or near atmospheric reflux temperature, this preferred method is referred to hereinafter as the "reflux-cool-reflux" or "RCR" method.

During the course of carrying out the vanadium reduction, the catalyst precursor forms. The precursor precipitates from the alcohol medium as a finely divided precipitate that contains the promoter elements after their addition. The promoted catalyst precursor slurry is recovered after cooling to below 50° C. by conventional techniques well known to those skilled in the art, including filtration, centrifugation, and decantation. The resulting promoted catalyst precursor precipitate when dried, has a powdery, free-flowing consistency in contrast to a caked residue normally obtained when the catalyst precursor is recovered by heating the solution to dryness.

The promoted vanadium-phosphorus oxide catalysts of the instant invention contain vanadium in the average valence state of from about +3.9 to +4.6 or simply 3.9 to 4.6. This average valence state is achieved when at least a portion of the pentavalent vanadium introduced into the reaction mixture is reduced to the +4 valence state. It is believed that as this reduction occurs, the reduced vanadium simultaneously reacts with the phosphorus present in reaction mixture to form the promoted vanadium-phosphorus oxide catalyst precursor. Useful methods for preparing the VPO precursor are described in U.S. Pat. No. 4,562,268, which is expressly incorporated herein by reference.

The recovered catalyst precursor is heated to remove free solvent, and then roasted at a temperature of from 150° to 275° C., preferably under vacuum, to remove a portion of the bound solvate that includes both water and alcohol. To avoid reaction of the alcohol with catalytically active vanadium sites, the drying is performed in an atmosphere of low or no oxygen content such as dry nitrogen. The precursor may be dried at a relatively modest temperature of, for example, 110° C. to 150° C., and then subjected to "post dry" treatment (roasting) at a temperature in the range of 200° C. to 275° C. Advantageously, the post dry treatment is carried out by fluidizing the precursor powder in an inert gas in the post dry temperature range. After the bed reaches the desired temperature, it is held at that temperature for a suitable period, for example 30 minutes to two hours, and thereafter an air/steam mixture is introduced, preferably on an incremental schedule to a maximum of 10–30% oxygen, after which the bed is cooled in an inert atmosphere to room temperature. The dried catalyst powder is then formed into any desired structure for reactor use with the aid of a die lubricant such as graphite. Typically, about 4 percent by weight graphite is mixed with the dried promoted catalyst powder. The resultant catalyst bodies (structures) are subjected to heat treatment as described below for transformation to active catalyst.

The dried precursor compound is generally defined as $$VO(M)_m HPO_4 \cdot aH_2O \cdot b(P_{2/c}O) \cdot n(\text{organics})$$

where M is tin, bismuth, antimony, germanium, titanium, zirconium, zinc, nickel, cerium, lanthanum, uranium, silicon or combinations thereof, m is a number from about 0.005 to about 0.1, preferably no greater than about 0.04, b is a number taken to provide a P/V atom ratio of from about 0.95 to about 1.3, and c is a number representing the oxidation number of phosphorus and has a value of 5.

Activation of the formed promoted catalyst is performed in a controlled manner using a sequence of gas and thermal treatments. The activated catalyst corresponds to the formula:

$$(VO)_2(M)_m P_2O_7 \cdot b(P_{2/c}O)$$

where M, m, b and c are as defined above. The overriding principle to follow in these treatments is to avoid treatments in which exotherms occurring on the catalyst surface as a result of either alcohol oxidation or phosphate condensation (i.e., catalyst phase changes) exceed by 30° to 50° C. or more the set point temperature of the furnace. Accordingly, a sequence of temperature holds are introduced at times when the catalyst shows exothermic behavior. Typically, the formed promoted catalyst is heated to 200° C. at 4° C./min. from ambient temperature in flowing air. After a one hour hold at 200° C., steam is added such that the air/steam ratio is between 0.50 and 1.50, preferably at 1.00. The ratio of the total flow of gas (air and steam) to the total weight of catalyst treated is generally between 10 and 20 L/min.-lbs., where the total gas flow is given in standard liters per minute and the weight of catalyst is in lbs. The catalyst is then heated in the air/steam flow while the temperature is increased at an average of 4° C./min. up to 425° C. The catalyst is heated at 425° C. for one hour, after which time the air is replaced with nitrogen and the catalyst is heated for another 6 hrs. in a nitrogen/steam flow at 425° C. The catalyst is then cooled to room temperature in a dry atmosphere.

More generally, the activation process may be described as follows. In operation of the process of the instant invention, the catalyst precursor is transformed into the active catalyst by a series of steps conveniently referred to as calcination. This transformation, which is critical for the preparation of superior catalysts, is accomplished in three stages. For convenience, these may be referred to as (1) initial heat-up stage; (2) rapid heat-up stage, and (3) maintenance/finishing stage.

In the initial heat-up stage, the catalyst precursor is heated in an atmosphere selected from the group consisting of air, steam, inert gas, and mixtures thereof, at any convenient heat-up rate, to a temperature not to exceed the phase transformation initiation temperature, which temperature is about 300° C. In general, suitable temperatures for the initial heat-up stage range from about 200° C. to about 300° C. with a temperature of from about 250° C. to about 275° C. being preferred.

After the desired temperature has been achieved in the initial heat-up stage, the initially selected atmosphere (in the event it does not contain molecular oxygen and steam and/or has a different composition than that which is desired for the rapid heat-up stage) is replaced by a molecular oxygen/steam-containing atmosphere, while maintaining the catalyst precursor at the temperature achieved in the initial heat-up stage. Such atmosphere optionally may contain an inert gas and, as such, may be conveniently represented by the formula $$(O_2)_x(H_2O)_y(IG)_z$$

wherein IG is an inert gas and x, y, and z represent mol % (or volume %) of the $O_2$, $H_2O$, and IG components, respectively, in the molecular oxygen/steam-containing atmosphere, with x having a value greater than zero (0) mol %, but less than 100 mol %, y having a value greater than zero (0) mol %, but less than 100 mol %, and z having a value representing the balance of the molecular oxygen/steam-containing atmosphere. A critical feature of the instant invention is that such atmosphere must contain at least a portion of molecular oxygen and water (as steam). The presence of the inert gas in such atmosphere, as indicated by the formula, is optional. Nonlimiting examples of inert gases suitable for use in the molecular oxygen/steam-containing atmosphere include (molecular) nitrogen, helium, argon, and the like, with nitrogen generally being preferred for practical reasons.

Once the molecular oxygen/steam-containing atmosphere is provided, the catalyst precursor is subjected to the rapid heat-up stage of the calcination. In the rapid heat-up stage, the initial heat-up stage temperature is increased at a programmed rate of from about 2° C. per minute (°C./min) to about 12° C./min, preferably from about 4° C./min to about 8° C./min, to a value effective to eliminate or remove the water of hydration from the catalyst precursor. In general, a temperature of from about 340° C. to about 450° C., usually at least about 350° C. and preferably from about 375° C. to about 425° C. is suitable.

Following the rapid heat-up stage, the catalyst precursor is subjected to the maintenance/finishing stage of calcination. In the maintenance/finishing stage, while the molecular oxygen/steam-containing atmosphere, is maintained, the temperature is adjusted to a value greater than 350° C., but less than 550° C., preferably from about 375° C. to about 450° C., most preferably from about 400° C. to about 425° C. The adjusted temperature is then maintained, first in the molecular oxygen/steam-containing atmosphere for a time effective to provide a vanadium oxidation state of from about +4.0 to about +4.5 or simply from about 4.0 to about 4.5, and thereafter in a nonoxidizing, steam-containing atmosphere for a time effective to complete the catalyst precursor-to-active catalyst transformation to yield the active catalyst. In a manner similar to the molecular oxygen/steam-containing atmosphere, the nonoxidizing, steam-containing atmosphere also optionally may contain an inert gas, with nitrogen generally being the preferred inert gas for practicable reasons.

The nonoxidizing, steam-containing atmosphere need not necessarily be completely free of molecular oxygen. However, such atmosphere preferably is substantially free of molecular oxygen. Accordingly, molecular oxygen may be present in an amount which is not effective to cause further oxidation of the vanadium beyond the desired oxidation state of about +4.0 to about +4.5, more particularly, not beyond the maximum desired oxidation state of about +4.5. In general, molecular oxygen may be present in amounts which do not exceed about 0.5 mol % of the nonoxidizing, steam-containing atmosphere.

It will be apparent to those skilled in the art that the period of time during which the adjusted temperature is maintained in the molecular oxygen/steam-containing atmosphere in order to provide the desired vanadium oxidation state of from about +4.0 to about +4.5 will depend to some extent upon the vanadium oxidation state achieved during the rapid heat-up stage, which, in turn, will depend to some extent upon the period of time during which the catalyst precursor material is exposed to the molecular oxygen/steam-containing atmosphere at the stated rapid heat-up stage temperatures. In general, a period of time of from about 0.25 hour to about 2 hours is suitable, with a period of time of from about 0.5 hour to about 1 hour being preferred.

A suitable period of time during which the adjusted temperature is maintained in the nonoxidizing, steam-containing atmosphere is at least 1 hour, although longer periods of time up to 24 hours, or longer, may be employed, if desired, with a period of time of from about 3 hours to about 10 hours being preferred, and a period of about 6 hours being most preferred.

After activation by the process described above, the catalyst is brought to full activity by contacting it with a stream of reactant gases comprising oxygen (typically air) and a n-butane or another suitable hydrocarbon gas, and reacting the hydrocarbon with oxygen in the presence of the catalyst for a period sufficient to equilibrate the catalyst. The equilibration process takes place at a temperature of at least 350° C., typically 385°–450° C. It is important that the stream contacting the catalyst contain at least about 0.6% n-butane during equilibration. Generally, equilibration requires several hundred hours, most typically 150 to 400 hours exposure to the reaction. The developed B.E.T. surface area of the catalyst after equilibration is typically at least about 10% greater than the B.E.T. surface area before equilibration. Where the catalyst is activated by the method described hereinabove, and the preferred promoter to vanadium ratios prevail, the catalyst exhibits a developed surface area of at least about 28 $m^2$/g. Developed B.E.T. surface areas of between about 28 and about 32 $m^2$/g are attainable in accordance with the process of the invention. Although n-butane is preferred, the equilibration can be carried out using other nonaromatic hydrocarbons containing at least four carbon atoms in a straight chain, e.g., 1-butene, 2-butene, 1,3-butadiene, pentenes, hexenes, heptenes, octenes, nonenes, decenes, and mixtures of these with or without saturated hydrocarbons such as n-butane, as long as the requisite unbranched C$_4$ hydrocarbon chain is present in the molecule.

It has been discovered that activity of the catalyst is further maximized if the equilibration is carried out substantially in the absence of any phosphorus compound in the gas stream. Preferably, however, a phosphorus compound is incorporated in the gas stream after the equilibration period to preserve the activity of the catalyst during manufacturing operations.

After activation and equilibration, the precursor is transformed to a catalyst comprising a substantial proportion of vanadyl pyrophosphate, a compound having the empirical formula (VO)$_2$P$_2$O$_7$. The presence of this compound may be identified by its characteristic X-ray diffraction pattern. Examples of diffraction patterns for various vanadyl pyrophosphate preparations are shown in FIG. 22B of Centi, Trifiro, Ebner and Franchetti, "Mechanistic Aspects of Maleic Anhydride Synthesis from C$_4$ Hydrocarbons over Phosphorus Vanadium Oxides," *Chemical Reviews*, 88, 55–80 (1988). Differences in the ratio of the height of the diffraction peak at d-spacing 3.86 Å (2$\theta$ value of 23.0°) to the height of the diffraction peak at d-spacing 3.14 Å (2$\theta$ value of 28.4°) are indicative of structural order differences in the various vanadyl pyrophosphate preparations. The selective oxidation of hydrocarbons with vanadium phosphorus oxide systems is described as a structure sensitive reaction, and thus sensibly depends upon the structure of the vanadyl pyrophosphate. In equilibrated shaped body catalysts having a volume >0.02 cc and containing a promoter effective to enhance activity while maintaining yield in the oxidation of C$_4$ hydrocarbons to maleic anhydride, it has been found that the most effective results are realized where the ratio of the height of the diffraction peak at d-spacing 3.86 Å (2$\theta$ value of 23.0°) to the height of the diffraction peak at d-spacing 3.14 Å (2$\theta$ value of 28.4°) is in the range of between about 0.8 to about 1.3, preferably <1.20.

The promoted catalysts of the instant invention possess a characteristically high intrinsic surface area which ranges from about 25 to 40 m$^2$/g. These surface areas are measured using Quantachrome Quantasorb instrument according to the single point BET method with nitrogen [from Brunauer et al., *Journal of the American Chemical Society*, 60, 309–319 (1939)]. It is believed that the use of promoters in accordance with the invention serves essentially to develop the intrinsic surface area possessed by the catalyst structure, not to materially alter the structure in a way that changes the intrinsic area.

The catalyst employed in the instant invention exhibits a phosphorus/vanadium atom ratio from about 0.95 to 1.30, a ratio of about 1.0 to about 1.2 being preferred, and a ratio of between about 1.05 and about 1.15 being most preferred. In general, the phosphorus/vanadium atom ratio in the catalyst is determined by the phosphorus/vanadium atom ratio in the starting catalyst that is charged to the reactor.

The promoted catalysts prepared in the instant invention are useful in a variety of reactors to convert non-aromatic hydrocarbons to maleic anhydride. The catalysts may be used in a fixed-bed reactor in the form of tablets, pellets, or the like, or in a fluid-bed reactor using catalysts preferably having a particle size of less than about 300 microns. Detail of the operation of such reactors are well known by those skilled in the art.

The promoted catalysts of the instant invention particularly are useful in fixed-bed (tubular), heat exchanger-type reactors. The tubes of such reactors can vary in diameter from about 0.635 cm (0.25 inch) to about 3.81 cm (1.5 inches) and the length can vary from about 15.24 cm (6 inches) to about 609.6 cm (20 feet) or more. It is desirable to have the surfaces of the reactors at relatively constant temperatures, and some medium to conduct heat from the reactors is necessary to aid in temperature control. Non-limiting examples of such media include Woods metal, molten sulfur, mercury, molten lead, and eutectic salt baths. A metal block reactor whereby the metal surrounding the tube acts as a temperature regulating body can also be used. The reactor or reactors can be constructed from iron, stainless steel, carbon steel, glass, and the like.

The reaction to convert non-aromatic hydrocarbons to maleic anhydride requires only contacting the hydrocarbons admixed with a molecular oxygen-containing gas (including molecular oxygen), such as air or molecular oxygen-enriched air, with the catalyst at elevated temperatures. In addition to the hydrocarbon and molecular oxygen, other gases such as nitrogen and steam, may be present or added to the reactant feedstream. Typically, the hydrocarbon is admixed with the molecular oxygen-containing gas, preferably air, at a concentration of about one mole percent to about 10 mole percent hydrocarbon and contacted with the catalyst at a space velocity of about 100 hr$^{-1}$ to about 4000 hr$^{-1}$ at a temperature between 300° C. and about 600° C., preferably 1500 hr$^{-1}$ and about 325° C. to about 425° C., to provide an excellent yield and selectivity to maleic anhydride.

The pressure is not critical in the reaction to convert non-aromatic hydrocarbons to maleic anhydride. The reaction may be conducted at atmospheric, superatmospheric, or subatmospheric pressure. It will generally be preferred, however, for practical reasons to conduct the reaction at or near atmospheric pressure. Generally, pressures of from about 1.013×10$^2$ kPa-G (14.7 psig, 1 atmosphere) to about 3.45×10$^2$ kPa-G (50 psig) may be conveniently employed.

Maleic anhydride produced by the catalysts of the instant invention may be recovered by any means well known to those skilled in the art. For example, maleic anhydride can be recovered by direct condensation or by absorption in suitable media with subsequent separation and purification of the anhydride.

A large number of non-aromatic hydrocarbons having from four to 10 carbon atoms can be converted to maleic anhydride using the catalysts of the instant invention. It is necessary that the hydrocarbon contain not less than four carbon atoms in a straight chain. As an example, the saturated hydrocarbon n-butane is satisfactory but isobutane (2-methyl-propane) is not satisfactory for conversion to maleic anhydride although its presence is not harmful. In addition to n-butane, other suitable hydrocarbons include the pentanes, the hexanes, the heptanes, the octanes, the nonanes, the decanes, and mixtures of any of these, with or without n-butane so long as an unbranched chain having no less than four carbon atoms is present in the saturated hydrocarbon molecule.

Unsaturated hydrocarbons are also suitable for conversion to maleic anhydride using the catalyst of the instant invention. Suitable unsaturated hydrocarbons include the butenes (1-butene and 2-butene), 1,3-butadiene, the pentenes, the hexenes, the heptenes, the octenes, the nonenes, the decenes, and mixtures of any of these with or without saturated hydrocarbons such as n-butane, as long as the requisite unbranched $C_4$ hydrocarbon chain is present in the molecule.

Cyclic compounds such as cyclopentane and cyclopentene are also satisfactory feed materials for conversion to maleic anhydride.

Of the aforementioned feedstocks, n-butane is the preferred saturated hydrocarbon and the butenes are the preferred unsaturated hydrocarbons, with n-butane being the most preferred of all feedstocks.

It will be noted that the aforementioned feedstocks need not necessarily be pure substances, but can be technical grade hydrocarbons.

The principal product from the oxidation of the aforementioned suitable feed materials is maleic anhydride although significant amounts of by-products may also be produced when the feedstock is a hydrocarbon containing more than four carbon atoms.

The equilibrated catalysts of the invention exhibit a weight/area productivity of at least about 3.5 mg maleic anhydride/$m^2$-hr and/or a weight/weight productivity of at least about 100 g maleic anhydride/kg.cat.-hr. when contacted with a gas containing 2.4% by volume n-butane in air, at a gas flow volume to catalyst weight ratio of 2180 cc/g-min. under a pressure of $1.055 \times 10^2$-kPa-G, and at a temperature sufficient to maintain a hydrocarbon conversion of 85 mole percent. When employed in a commercial fixed bed maleic anhydride reactor after equilibration, the catalyst may continue to exhibit its maximum productivity for a substantial period of time. Eventually, the activity and productivity of the catalyst begin gradually to deteriorate, but a catalyst of the invention that has been equilibrated continues to exhibit productivities in excess of the above noted minimums for a substantial period, typically 1000 to 2000 hours, following equilibration. Thus, the catalysts of the invention offer substantial advantages in the commercial manufacture of maleic anhydride.

The following examples illustrate the best currently-known method of practicing this invention.

EXAMPLE 1

A five liter, round bottom flask, fitted with a paddle stirrer, a thermometer, a heating mantle and a reflux condenser was charged with isobutyl alcohol (3400 ml), oxalic acid (141.9 g), and $V_2O_5$ (318.3 g), to which was added $H_3PO_4$ (373.2 g; 105.7%). The resulting mixture was then refluxed for 5–6 hours to give a bright blue mixture, cooled to 30°–70° C., and then zirconium was added (for quantities see PREP TABLE 1) as $Zr(C_4H_9O)_4.C_4H_9OH$ solution with $\approx 200$ ml isobutyl alcohol. The mixture was heated again to reflux and held for an additional six hours. After cooling to room temperature, the blue solid was separated by vacuum filtration, and dried between 110° C. and 150° C. in a nitrogen purged vacuum oven (23/24 in Hg). The VPO precursor prepared in this manner has a P/v ratio of 1.15.

TABLE 1

| Catalyst No. | PREP GMS of Zr Butoxide | Zr/V Ratio |
|---|---|---|
| 1A | 0 | 0 |
| 1B | 8.01 | .005 |
| 1C | 16.02 | .01 |
| 1D | 32.05 | .02 |
| 1E | 60.1 | .0375 |

EXAMPLE 2

A two liter, round bottom flask, fitted with a paddle stirrer, a thermometer, a heating mantle and a reflux condenser was charged with of isobutyl alcohol (1360 ml), oxalic acid (56.75 g) and $V_2O_5$ (127.32 g) to which was added $H_3PO_4$ (168.74 g; 105.7%). The resulting mixture was then refluxed for 3 hours to give a bright blue mixture, cooled to 30°–70° C., and then zirconium was added as $Zr(C_4H_9O)_4.C_4H_9OH$ solution (48.08 g). The reaction mixture was heated again to reflux and held for an additional 13 hours. After cooling to room temperature, the blue solid was separated by vacuum filtration, and dried between 110° C. and 150° C. in a nitrogen purged vacuum oven (23/24 in Hg). The VPO precursor (2A) prepared in this manner has a P/V ratio of 1.30 and a Zr/V ratio of 0.075.

EXAMPLE 3

The catalyst precursor powders (1A through 1E and 2A) were treated in the following general fashion: About 100 gms of the individual powder was loaded into a 1' OD stainless steel tube with $\frac{1}{8}$" centered thermocouple well, and the powder was fluidized with about 900 cc STP/min nitrogen gas. The powder bed temperature was raised to 260° C. and held for one hour at which time a 50:50 steam:air mixture was introduced incrementally such that the powder was treated with 1.32% oxygen for 20 minutes, 2.625% oxygen for 20 minutes, 5.25% oxygen for 20 minutes, 10.5% oxygen for 60 minutes, and then 100% nitrogen during the cool down to room temperature. Using powder produced in the above fashion, 5/32" diameter trilobe shaped tablets were formed using a Stokes 512 Rotary Tableting machine.

EXAMPLE 4

Catalyst tablets 1A through 1E and 2A (about 18–20 grams of each) were placed into a box oven purged with nitrogen gas and heated to approximately 250° C., at which point the atmosphere in the oven was changed to a mixture of 25 volume percent nitrogen, 25 volume percent air and 50 volume % steam. The temperature was raised at a controlled rate of 4° C./min to $\approx 425$° C. and held there for $\approx 1$ hour, then the atmosphere in the oven was changed to 50 volume percent nitrogen and 50 volume percent steam for six hours. The tray of catalyst structures was then allowed to cool to room temperature while purging the oven with dry nitrogen. (Note: For good activation it was found critical to control exotherms from air introduction such that catalyst temperatures did not significantly exceed 300° C. prior to the controlled temperature ramp. This was accomplished by holding the oven at constant temperature until exothermic activity caused by oxygen introduction subsided).

EXAMPLE 5

To determine and compare the catalyst efficiency in terms of activity as measured by reaction temperature and reaction yield of maleic anhydride from n-butane, catalyst structures (bodies) (about 12 g) were placed in a 0.43" inside diameter stainless steel reactor, and this catalyst was fed $2.4\pm 0.2$% butane in synthetic air (21% oxygen and 79% helium) at 15 psig and 1500 GHSV. The reaction temperatures and reaction yields reported in Table 2 were obtained when the catalysts were running at $85\pm 2$% butane conversion after 200–400 hours on stream time. The conversions and yields reported in Table 2A were obtained when the catalysts were running at a constant bath temperature of about 383° C. after 200–400 hours on-stream time.

after which time the bright blue reaction mixture was allowed to cool to room temperature.

The solid was recovered by vacuum filtration on 24-cm filter paper. The wet cake was transferred to two

TABLE 2

CATALYST PERFORMANCE TABLE

| EX | Zr/V RATIO | OST (HRS) | BATH °C. | % CV | % Yield | % C Tls. | SA[1] m²/g | wt./wt. Prod., g-MAn/kg-Cat.-hr. | wt./area Prod., mg-MAn/m2 Cat.-hr. | Cat.Den. g-Cat./-cc-Cat. |
|---|---|---|---|---|---|---|---|---|---|---|
| 1A | 0.00  | 335 | 395 | 85.6 | 57.3 | 98.3 | 23.4 | 131.27 | 5.61 | 0.672 |
| 1B | 0.005 | 250 | 400 | 85.3 | 56.8 | 96.8 | 25.7 | 130.12 | 5.06 | 0.722 |
| 1C | 0.01  | 308 | 377 | 85.1 | 57.3 | 97.2 | 31.0 | 131.27 | 4.23 | 0.478 |
| 1D | 0.02  | 251 | 387 | 85.6 | 56.2 | 98.8 | 30.3 | 128.75 | 4.25 | 0.518 |
| 1E | 0.038 | 240 | 384 | 84.7 | 57.3 | 97.8 | 28.9 | 131.27 | 4.54 | 0.585 |
| 2A | 0.075 | 250 | 394 | 85.2 | 57.2 | 98.1 | 27.2 | 131.04 | 4.82 | 0.650 |

[1]Surface area of the catalyst was measured after the reactor run.

TABLE 2A

| EX | Zr/V RATIO | OST (HRS) | BATH °C. (±3) | % CV | % Yield | % C Tls. | SA, m²/g | wt./wt. Prod., g-MAn/kg-Cat.-hr. | wt./area Prod., mg-MAn/m2-Cat.-hr. | Cat.Den. g-Cat./-cc-Cat. |
|---|---|---|---|---|---|---|---|---|---|---|
| 1A | 0.00  | 343 | 383 | 70.0 | 51.6 | 98.0 | 23.4 | 117.62 | 5.03 | 0.695 |
| 1B | 0.005 | 259 | 383 | 74.5 | 52.9 | 98.2 | 25.7 | 119.80 | 4.66 | 0.685 |
| 1C | 0.01  | 312 | 383 | 84.8 | 58.4 | 99.3 | 31.0 | 133.66 | 4.31 | 0.500 |
| 1D | 0.02  | 259 | 383 | 81.6 | 56.8 | 98.3 | 30.3 | 129.77 | 4.28 | 0.517 |
| 1E | 0.038 | 240 | 384 | 84.7 | 57.3 | 97.8 | 28.9 | 115.79 | 4.01 | 0.585 |
| 2A | 0.075 | 259 | 383 | 84.1 | 55.9 | 99.0 | 27.2 | 127.75 | 4.70 | 0.627 |

As the data in the above table indicate, the catalysts prepared with zirconium promoter exhibit significantly higher activity over a narrow range of zirconium concentrations. Also, the surface area is considerably higher in these cases.

EXAMPLE 6

Catalysts of this invention comprise shaped forms that possess a volume of at least about 0.02 cc. It has been discovered that when vanadium-phosphorus oxide powder is promoted with certain elements and formed into shaped tablets, the tablets exhibit an increased BET surface area after equilibration in a butane-oxygen gas stream for about 150 hours or more at temperatures sufficient to lead to about 80% conversion of butane over that of the surface area measured on the same shaped tablets when no promoter elements are present. Unpromoted vanadium-phosphorus oxide shaped forms do not exhibit a change in surface area after exposure to a butane-oxygen gas stream in which conversions of at least about 80% are achieved. However, if the unpromoted powder is compressed into higher density forms then broken into small irregular granules such that the exposed geometric surfaces are not those formed by compression against punch and die tooling, then an increase in surface area does occur upon exposure to a butane-oxygen gas stream at temperatures in which butane conversions of about 80% are obtained. This example illustrates the surface area increase for granules of vanadium-phosphorus oxide powder.

To a 3-liter, round bottom flask equipped with a mechanical stirrer with Teflon paddle, water-cooled reflux condenser, thermometer, and heating mantle, was charged 1365.6 g of isobutyl alcohol, 86.4 g of oxalic acid dihydrate), 193.5 g of vanadium pentoxide ($V_2O_5$), and 227.7 g of 105.3% phosphoric acid (solution P/V=1.15). The stirred mixture was heated to a reflux temperature of 98° C. over a period of six hours. The heating continued with a timer on the Variac heating mantle voltage controller for a period of 10 hours more, quartz boats and dried in vacuum oven at 150° C. under 22 mm Hg vacuum with nitrogen purge. The dried solids were sieved to below 16 mesh (1.0 mm), then further dried under 40 SLPM (standard liters per minute) nitrogen purge in a Thermolyne oven while ramping at 2° C./min. the temperature from ambient to 260° C. with a 2-hr. hold at 260° C.

The gray-green powder was mixed with 4 weight percent graphite and pressed to produce ⅛" cylindrical pellets with an average bulk density of 1.37 g/cc. The pellets were then crushed and sieved to 10 to 16 mesh (1.0 to 1.7 mm) granules.

The granular sample was transferred to trays with at least 40% open area. The trays were placed inside a controlled atmosphere oven. For lab batch sizes of about 6 lbs. or less, air was passed through the oven at 20 SLPM while ramping at 4° C./min. to 425° C. The ramping rate was measured through the use of thermocouples in individual catalyst trays on a periodic basis to check the temperature characteristics. The temperature was held at 275° C. for 1 hr. in order to achieve a uniform temperature in the trays. At the end of the 275° C. hold, steam was added at 20 SLPM (high purity water vaporized at a rate of 0.25 gallon/hr.), so the overall oven atmosphere was 50:50 air:steam. Proper activation of the catalyst occurs if the flow/weight ratio, F/W in units of ft³/min.-lb.-catalyst, is between 0.16 and 0.31. After a temperature of 425° C. was reached, the oven was maintained at that temperature for 7 hrs. After 1 hr. at 425° C., the 20 SLPM air was replaced with 20 SLPM dry nitrogen with the steam flow rate still at 20 SLPM (0.25 gallons/hr. of water feed). The 50:50 nitrogen:steam treatment continued for 6 hrs. more at 425° C. After the steam was shut off, the activated catalyst was cooled to room temperature in nitrogen. The above procedure is referred to as "air-nitrogen-steam" activation or ANST treatment. The catalyst granules were found to lose about 10% of their original weight after the above activation treatment. The color changed from black to gray-green. The B.E.T. surface area of the treated catalyst was 20.2 m²/g.

Catalyst were evaluated for n-butane oxidation performance using 11.7 g of 1.0–1.7 mm granules in a ½" outside diameter stainless steel microreactor immersed in a fluidized sand bath. Catalyst no. 3 was treated for about 24 hrs. in 1.5 mole percent n-butane-in-oxygen gas stream at a space velocity of 1150 hr$^{-1}$ at a temperature of 375° C. and a reactor pressure of $1.055 \times 10^2$ kPa-G (15.3 psig). The n-butane conversion was adjusted to about 88% at this time. The space velocity was then raised to 1500 hr$^{-1}$ and the n-butane concentration increased to 2.4 mole percent. The n-butane conversion was adjusted to about 85% by adjusting the sand bath temperature. After about 100 and 200 hrs. of on-stream time, the catalyst produced averaged performance results (bath temperature, conversion, selectivity, yield) shown in Table 3. The BET surface area was measured on the catalyst granules after evaluation in a butane-oxygen gas containing stream.

dies with punches necessary to produce three-grooved cylinders having a 3.97 mm diameter and 3.97 mm in length. The side crush strength of these tablets was adjusted to around 6.5 lbs.

The black cylinders produced by the above procedure were ANST treated as described in Example 6. The grey-green cylinders were designated as catalyst no. 4. Catalyst properties and reactor performance data are given in Table 4.

Promoted catalysts were prepared on scales from 3 to 12 liters with M/V ratios from 0.01 to 0.06. To a 12-liter, round bottom flask fitted with mechanical stirrer with Teflon paddle, water-cooled Friedrich condenser with mineral oil bubbler connected to a house nitrogen supply, thermometer, and heating mantle was charged 5703 g IBA, 345 g oxalic acid dihydrate, 774 g V$_2$O$_5$, and 904 g of 106.1% H$_3$PO$_4$ with 240 g IBA as a rinse. A reflux-cool-reflux "RCR" procedure was followed.

In preparation of a Bi-promoted catalyst, after 6 hrs. at reflux temperature, a solution of 28% Bi 2-ethylhexano-

TABLE 3

| Cat. No. | P/V | SA, m²/g | OST, Hrs. | Bath, °C. | CV, % | Selectivity % | Yield % | wt./wt. Prod., g-MAn/kg-Cat.-hr. | wt./area Prod., mg-MAn/m2 Cat.-hr. | Cat. Den., g-Cat./cc-Cat. |
|---|---|---|---|---|---|---|---|---|---|---|
| 3 | 1.00 | 31.9 | 200 | 399 | 87.3 | 69.2 | 60.4 | 130.07 | 4.08 | 0.731 |

EXAMPLE 7

Commercial fixed-bed reactors employ various tabletted shapes of maleic anhydride catalysts for the conversion of n-butane. A discussion of the advantages of specific catalyst shapes is given in a pending application Ser. No. 07/812,252 (Shaped Oxidation Catalyst Structures for the Production of Maleic Anhydride) filed Dec. 20, 1991 by the common assignee which application is a continuation of Ser. No. 07/592,722, now abandoned. This example compares reactor data for unpromoted open cell vanadium-phosphorus oxide catalyst with that for samples of promoted open cell vanadium-phosphorus oxide catalysts of the invention and other promoted open cell catalyst, in which, for all catalysts, the powder was tabletted as three-grooved cylinders of 3.97 mm in diameter and 3.97 mm in length.

For preparation of the unpromoted catalyst, a 12-liter round bottom flask fitted with mechanical stirrer with Teflon paddle, a water-cooled Friedrich condenser with mineral oil bubbler was connected to a house nitrogen supply, a thermometer, and a heating mantle. To the flask was charged 6423 g IBA, 345 g oxalic acid dihydrate, 774 g V$_2$O$_5$, and 904 g of 106.1% H$_3$PO$_4$ with 240 g IBA as a rinse. The stirred slurry was heated to 95° C. at which time the mixture changed from dark green to a lighter green with the appearance of the blue catalyst precursor phase. The heating was continued for a total of 16 hrs.

The cooled slurry was suction-transferred to a 4-L filter flask then divided among two 24-cm filter papers in porcelain filter funnels. The wet cakes were transferred to three Pyrex baking pans which were placed in a Fisher Isotemp vacuum oven for drying up to 260° C. The dried powder was sieved to below 16 mesh.

The powder was blended with 4 weight percent graphite and densified on a Stokes 512 Rotary Tableting press equipped with dies and punches necessary to form ¼" cylindrical pellets having a bulk density of around 1.35 g/cc. The pellets were ground and resieved to produce powder with 18 to 30 mesh particle size. The powder was then fed on the rotary tableting press into ate (sold under the trade designation "Bi Hex-Cem" by Outokumpu/Mooney Chemicals, Inc., Cleveland, Ohio (hereinafter "OM Group, Inc.")) dissolved in 480 g IBA was added dropwise to the cooled slurry. The resulting system was returned to reflux for a 10-hr. period, and the precipitated Bi-VPO precursor then recovered by filtration and processed into 3.97 mm grooved cylinders (Length/Diameter=1) by the procedure given above for the unpromoted sample. The cylinders were ANST treated as described in Example 6. The catalyst obtained was designated as no. 12. Catalyst properties and reactor performance data are given in Table 4 for tests at 85% conversion. Table 4A records the data for operation at a constant bath temperature of 383° C.

Other promoter elements were used to prepare 5/32" grooved cylinders that were ANST treated. In all cases alkylcarboxylate salts of the metal ions were used diluted with either isobutyl alcohol, decane, isobutyl isobutyrate, or mineral spirits (whichever produced a soluble mixture without precipitation). The promoter salts included K Hex-Cem, Li Ten-Cem, Ca Hex-Cem, Ni Hex-Cem, La Hex-Cem ("Rare Earth Hex-Cem"), Ce Hex-Cem, and Sn Hex-Cem ("Hex-Cem" is the OM Group, Inc. designation for the 2-ethylhexanoate salts and "Ten Cem" is the OM Group, Inc. designation for the neodecanoate salt of the indicated metal, in each instance, diluted with mineral spirits). In addition to catalyst no. 12 described above, the various promoter salts produced activated catalysts numbered 5 through 16 as shown in Tables 4 and 4A. Catalysts 8, 11, 14, and 16 gave less satisfactory combinations of yield and bath temperature than did other catalysts of the invention. In this set of runs, using the particular reactor of this example, the preferred performance criteria were a yield of at least 57% and a bath temperature of less than 400° C. Thus, in Tables 4 and 4A, samples marked with asterisks are examples of promoters (5, 6, 8, and 15) or amounts of promoters (13) that are not part of this invention. As seen by examination of the tabletted catalysts in Tables 4 and 4A, the promoted samples show equal or better reactor performance compared to the unpromoted sample with the additional benefit of lower temperature operation by some 15° to 25° C. after 150 to 350 hrs. of on-stream time. This feature has clear commercial benefits in terms of lower temperature operation and enhanced catalyst life in a fixed-bed salt bath reactor.

the stirred solution. The mixture was refluxed for 5 hr. and cooled to room temperature. A mixture of 284 g of 105.7% of $H_3PO_4$, 241 g isobutyl alcohol, and 16.1 g of water were added to make a 100% $H_3PO_4$ solution. This solution was added dropwise to the 3-L flask. The dark green solution produced a pea green precipitate, and the

TABLE 4

| Cat. No., Promoter | M/V Ratio | Surface Area | | OST, Hr. | Bath, °C. | %-CV | %-Sel. | %-Yld. | %-C Tls. | Wt.-Wt. Prod., g-MAn/kg-Cat.-hr. | Wt.-Area Prod., mg-MAn/m2-Cat.-hr. | Cat. Den., g-Cat./cc-Cat. |
|---|---|---|---|---|---|---|---|---|---|---|---|---|
| | | m2/g | %-Inc. | | | | | | | | | |
| 4, None | 0.00 | | | 99 | 410 | 85.3 | 69.5 | 59.3 | 99.9 | 113.44 | 4.91 | 0.669 |
| | 0.00 | 26.6 | 0.0 | 182 | 409 | 85.0 | 69.3 | 58.8 | 97.6 | 113.63 | 4.92 | 0.669 |
| 5*, K Hex-Cem | 0.01 | | | 100 | 421 | 85.0 | 54.2 | 46.0 | 99.1 | 106.49 | 3.97 | 0.680 |
| | 0.01 | 26.8 | 0.7 | 201 | 425 | 85.6 | 49.3 | 42.2 | 98.5 | 97.70 | 3.65 | 0.680 |
| 6*, Li Ten-Cem | 0.01 | | | 91 | 410 | 85.5 | 66.0 | 56.4 | 97.8 | 121.46 | 4.50 | 0.731 |
| | 0.01 | 27.0 | 1.5 | 256 | 387 | 85.3 | 62.6 | 53.4 | 97.0 | 115.00 | 4.26 | 0.731 |
| 7*, Ca Hex-Cem | 0.01 | | | 98 | 405 | 85.9 | 66.3 | 57.0 | 98.9 | 139.63 | 4.93 | 0.643 |
| | 0.01 | 28.3 | 6.0 | 140 | 401 | 86.3 | 64.7 | 55.9 | 97.5 | 136.94 | 4.84 | 0.643 |
| 8*, Ba Hex-Cem | 0.009 | | | 91 | 410 | 85.5 | 66.0 | 56.4 | 97.8 | 121.46 | 3.65 | 0.731 |
| | 0.009 | 33.3 | 20.1 | 256 | 387 | 85.3 | 62.6 | 53.4 | 97.0 | 115.00 | 3.45 | 0.731 |
| 9, Zn Hex-Cem | 0.01 | | | 96 | 413 | 86.9 | 68.0 | 59.1 | 98.1 | 136.82 | 4.62 | 0.680 |
| | 0.01 | 29.6 | 10.1 | 206 | 396 | 85.4 | 69.0 | 58.9 | 97.7 | 136.36 | 4.61 | 0.680 |
| 10, Ni Hex-Cem | 0.02 | | | 103 | 400 | 85.2 | 70.4 | 60.0 | 99.1 | 153.44 | 5.05 | 0.616 |
| | 0.02 | 30.4 | 12.5 | 350 | 393 | 85.2 | 68.6 | 58.6 | 97.6 | 149.86 | 4.93 | 0.616 |
| 11, La Hex-Cem | 0.01 | | | 105 | 405 | 85.6 | 67.7 | 58.0 | 99.7 | 132.71 | 4.35 | 0.688 |
| | 0.01 | 30.5 | 12.8 | 201 | 405 | 84.4 | 66.4 | 56.1 | 97.9 | 128.37 | 4.21 | 0.688 |
| 12, Bi Hex-Cem | 0.01 | | | 96 | 415 | 85.5 | 69.1 | 59.1 | 100.3 | 145.76 | 5.03 | 0.688 |
| | 0.01 | 29.0 | 8.3 | 522 | 383 | 85.0 | 68.6 | 58.3 | 97.1 | 135.23 | 4.66 | 0.688 |
| 13*, Bi Hex-Cem | 0.06 | | | 113 | 405 | 85.0 | 65.5 | 55.6 | 99.9 | 112.26 | 4.40 | 0.780 |
| | 0.06 | 25.5 | 4.3 | 200 | 406 | 84.3 | 64.5 | 54.3 | 98.2 | 109.63 | 4.30 | 0.780 |
| 14, Ce Hex-Cem | 0.01 | | | 90 | 402 | 86.8 | 68.5 | 59.5 | 100.6 | 148.96 | 4.76 | 0.629 |
| | 0.01 | 31.3 | 15.0 | 162 | 406 | 84.2 | 68.5 | 57.7 | 98.7 | 144.45 | 4.62 | 0.629 |
| 15*, Ce + Sn Hex-Cems | 0.01 | | | 104 | 398 | 85.8 | 66.9 | 57.4 | 97.6 | 131.34 | 4.85 | 0.688 |
| | 0.01 | 27.1 | 1.8 | 140 | 409 | 85.5 | 67.2 | 57.5 | 97.7 | 131.57 | 4.85 | 0.688 |
| 16, Sn Hex-Cem | 0.01 | | | 62 | 409 | 85.2 | 68.1 | 58.0 | 97.6 | 128.03 | 3.67 | 0.713 |
| | 0.01 | 34.9 | 23.8 | 315 | 389 | 86.1 | 64.7 | 55.7 | 97.8 | 125.82 | 3.61 | 0.713 |

TABLE 4A

| CAT. NO., PROMOTER | M/V RATIO | SA | | OST, Hr. | Bath °C. (±3) | % CV | % Sel. | % Yield | %-C Tls. | wt./wt. Prod., g-MAn/kg-Cat.-hr. | wt./area Prod., mg-MAn/m2-Cat.-hr. | Cat.Den. g-Cat./cc-Cat. |
|---|---|---|---|---|---|---|---|---|---|---|---|---|
| | | m2/g | % Inc. | | | | | | | | | |
| 4,None | 0.00 | 26.6 | 0.0 | 185 | 383 | 60.9 | 77.2 | 47.0 | 97.8 | 108.26 | 4.07 | 0.674 |
| 5,K Hex-Cem | 0.01 | 26.8 | 0.7 | 210 | 383 | 52.3 | 68.9 | 36.1 | 97.4 | 82.61 | 3.08 | 0.695 |
| 6,Li Ten-Cem | 0.01 | 27.0 | 1.5 | 261 | 383 | 82.4 | 64.6 | 53.2 | 98.5 | 120.97 | 4.48 | 0.695 |
| 7,Ca Hex-Cem | 0.01 | 28.3 | 6.0 | 150 | 383 | 74.6 | 72.1 | 53.8 | 98.6 | 123.22 | 4.35 | 0.627 |
| 8,Ba Hex-Cem | 0.009 | 33.3 | 20.1 | 261 | 383 | 71.2 | 72.6 | 51.9 | 98.7 | 118.18 | 3.55 | 0.706 |
| 9,Zn Hex-Cem | 0.01 | 29.6 | 10.1 | 215 | 383 | 75.3 | 72.5 | 54.6 | 98.3 | 124.29 | 4.20 | 0.674 |
| 10,Ni Hex-Cem | 0.02 | 30.4 | 12.5 | 354 | 383 | 77.9 | 71.5 | 55.6 | 98.8 | 127.82 | 4.20 | 0.636 |
| 11,La Hex-Cem | 0.01 | 30.5 | 12.8 | 209 | 383 | 79.8 | 68.7 | 54.8 | 98.8 | 127.02 | 4.16 | 0.685 |
| 12,Bi Hex-Cem | 0.01 | 29.0 | 8.3 | 527 | 383 | 74.9 | 74.4 | 55.7 | 99.1 | 127.78 | 4.41 | 0.654 |
| 12A,Bi Hex-Cem | 0.01 | 27.4 | 2.9 | 531 | 383 | 84.5 | 69.6 | 58.8 | 97.4 | 134.70 | 4.92 | 0.674 |
| 13,Bi Hex-Cem | 0.06 | 25.5 | 4.3 | 211 | 383 | 71.5 | 69.1 | 49.4 | 98.2 | 114.31 | 4.48 | 0.767 |
| 14,Ce Hex-Cem | 0.01 | 31.3 | 15.0 | 173 | 383 | 78.4 | 69.1 | 54.2 | 98.7 | 125.35 | 4.00 | 0.695 |
| 15,Ce + Sn Hex-Cem | .01 | 27.1 | 1.8 | 151 | 383 | 69.5 | 74.3 | 51.6 | 97.9 | 118.85 | 4.39 | 0.674 |
| 16,Sn Hex-Cem | 0.01 | 34.9 | 23.8 | 319 | 383 | 82.6 | 66.6 | 55.0 | 98.6 | 126.15 | 3.61 | 0.674 |

EXAMPLE 8

Although the catalysts of this invention may be prepared by the general procedures given in U.S. Pat. Nos. 4,562,268 and 4,560,674, other patent procedures may also be adapted to produce promoted shaped catalyst forms of this invention. Katsumoto et al. in U.S. Pat. 4,132,670, example 2, describe the preparation of vanadium-phosphorus oxide from a mixture of isobutyl alcohol and benzyl alcohol.

An unpromoted catalyst sample of vanadium-phosphorus oxide was prepared by charging a mixture of 723 g isobutyl alcohol and 627 g of benzyl alcohol to a 3-Liter 3-necked round bottom flask equipped with mechanical stirrer, reflux condenser, and thermometer. Micronized $V_2O_5$ (below 10 mµ, 232 g) was added to resulting slurry was refluxed further for 20 hr. After about 1 hr., the slurry converted to a bright blue color and remained this color throughout the remainder of the reflux period. The slurry was cooled to room temperature and filtered. The wet cake was vacuum dried to 260° C. for about 6 hr. The dried solid was sieved below a 1.00 mm screen and 4% by weight graphite was added. The mixed solids were tableted to ½" cylinders having a density of about 1.40 g/cc. These cylinders were ground to below a 1.00 mm screen and used as tablet feed for 3.97 mm cylinders having three equidistant grooves along the longitudinal axis of the cylinder. The tableted sample was activated using the general ANST procedure described in Example 6 except that variable amounts of air were added to control exotherms (as measured by thermocouples embedded in 2×2" baskets holding the sample), holds at 240° C. and 275° C. were used to stabilize the samples thermally prior to ANST treatment to 425° C. in 25% air/25% nitrogen/50% steam. Both monolayered and packed baskets of samples were activated by this procedure. The monolayered unpromoted vanadium-phosphorus oxide sample is designated catalyst no. 17.

Bismuth promoted samples of the above catalyst were prepared at the 3-L scale by following the procedure above for the unpromoted vanadium-phosphorus oxide. After 5 hrs. at reflux for the bright blue slurry, the mixture was cooled to room temperature. To the cooled slurry was added dropwise 19.0 g bismuth 2-ethylhexanoate (28% Bi, Bi/V=0.01) dissolved in 92 g IBA. After addition, the blue slurry was refluxed for another 15 hrs., filtered, dried, and worked up identically to the unpromoted catalyst above. The ANST activated sample (both basketed and monolayered samples were obtained with the monolayered sample evaluated in a microreactor for butane oxidation as described in example 6) was designated catalyst no. 18.

The results of the tests of this example as conducted at constant conversion are set forth in Table 5 and the results of the tests conducted at constant temperature are set forth in Table 5A.

range. Tablets of 3/16" diameter with 1/16" core holes were made with a rotary tableting press having an average tablet weight of 0.151 grams and a length of 0.169 inches.

Two activation methods were used to generate the final catalyst. The first method followed that prescribed in U.S. Pat. No. 4,251,390 (i.e., "standard conditioning"). The catalyst was ramped at 10° C./minute from 250° C. to 425° C. in a 1.0% butane-in-oxygen-containing gas stream at a gas hourly space velocity (GHSV) of 1150/hr. After 21 hrs. of on-stream time, the butane level was increased to 1.5%; the measured butane conversion ranged from 75 to 84% during the next 19 hrs. After 40 hrs., the patent specified start-up procedure was abandoned and the butane level was further increased to 2.4% with the space velocity increased from 1500 to 1600/hr. for the cumulative total of 235 hrs. on-stream time. Catalyst performance data are shown in Table 6 for this catalyst designated as catalyst no. 19.

In the second activation method, the 3/16" cylindrical tablet with a 1/16" core hole was air-nitrogen-steam (ANST) treated as described in Example 6. The gray tablets were evaluated in a 0.43" inside diameter fixed bed reactor located within a fluidized sand bath. The catalyst was ramped from 375° C. to 415° C. in 2.4%

TABLE 5

| Cat. No., Promoter | M/V Ratio | SA, m²/g | % Inc. | OST, Hr. | Bath °C. | %-CV | % Selectivity | % Yield | %-C Tls. | wt./wt. Prod., g-MAn/m2-Cat.-hr. | wt./area Prod., mg-MAn/m2-Cat.-hr. | Prod., g-Cat./-cc-Cat. |
|---|---|---|---|---|---|---|---|---|---|---|---|---|
| 17, None | 0.00 | | | 103 | 416 | 86.2 | 68.6 | 59.4 | 98.3 | 166.30 | 6.05 | 0.563 |
| | 0.00 | 27.5 | 0.0 | 345 | 402 | 85.2 | 68.5 | 58.3 | 99.0 | 163.22 | 5.94 | 0.563 |
| 18, Bi Hex-Cem | 0.01 | | | 99 | 408 | 86.1 | 68.2 | 58.7 | 99.1 | 170.66 | 5.77 | 0.542 |
| | 0.01 | 29.6 | 7.1 | 289 | 395 | 85.7 | 67.9 | 58.2 | 98.0 | 169.21 | 5.72 | 0.542 |

TABLE 5A

| CAT. NO., PROMOTER | M/V RATIO | SA, m²/g | % Inc. | OST, Hr. | Bath °C. (±3) | % CV | % Sel. | % Yield | %-C Tls. | wt./wt. Prod., g-MAn/kg-Cat.-hr. | wt./area Prod., mg-MAn/m2-Cat.-hr. | Cat.Den. g-Cat./-cc-Cat. |
|---|---|---|---|---|---|---|---|---|---|---|---|---|
| 17,None | 0.00 | 27.5 | 0.0 | 355 | 383 | 70.0 | 73.9 | 51.7 | 98.2 | 118.14 | 4.30 | 0.571 |
| 18,Bi Hex-Cem | 0.01 | 29.6 | 7.1 | 296 | 383 | 75.0 | 71.6 | 53.9 | 98.3 | 122.88 | 4.15 | 0.549 |

EXAMPLE 9

Not all vanadium-phosphorus oxide catalysts result in high surface area products when prepared from isobutyl alcohol with the addition of beneficial amounts of promoter elements. U.S. Pat. Nos. 4,251,390; 4,283,307; and 4,560,674 describe the preparation of a lithium-zinc promoted vanadium-phosphorus oxide catalyst from an isobutyl alcohol-hydrochloric acid solution. The lithium/vanadium ratio was 0.002 and the zinc/vanadium ratio was 0.01.

U.S. Pat. No. 4,560,674, example 14 was followed exactly to generate 2364 grams of 260° C. dried powder. The powder was slugged to 1.9 g/cc as ½" slugs which were then ground to give 60% in the 18 to 30 mesh size butane in synthetic air (21% oxygen and 79% helium) over 18 hrs. at a GHSV value of 1500 to 1600/hr. The catalyst was evaluated for 167 hrs. of on-stream time and gave the performance data for catalyst no. 20 in Table 6.

TABLE 6

| CAT. NO., PROMOTER | M/V RATIO | M= | SA, m²/g | OST, Hr. | Bath °C. | % CV | % Sel. | % Yield | %-C Tls. | wt./wt./ Prod., g-MAn/kg-Cat.-hr. | wt./area Prod., mg-MAn/m2-Cat.-hr. | Cat.Den. g-Cat./-cc-Cat. |
|---|---|---|---|---|---|---|---|---|---|---|---|---|
| 19, Li + Zn | 0.01 0.002 | Zn Li | 15.9 | 233 | 449 | 85.0 | 56.4 | 48.0 | 98.7 | 93.50 | 5.88 | 0.873 |
| 20, Li + Zn | 0.01 0.002 | Zn Li | 8.6 | 167 | 492 | 85.3 | 50.8 | 43.3 | 98.5 | 93.25 | 10.84 | 0.780 |

EXAMPLE 10

Catalysts of this invention typically are used in tubular reactors having dimensions of 2.10 cm inside diamter and 600 cm long. Catalyst packs for two of these reactors were made up from 5/32" grooved cylinders from Example 7, catalyst nos. 4 and 12. The catalyst packs included a stratified zone with 20 weight-% Al₂O₃ dilution that spanned 100 to about 230 cm of bed depths in the 600-cm long reactors.

Each catalyst pack was brought on-stream with 1.5% butane feed at 1150/hr. gas hourly space velocity (GHSV) and 2.0 to 2.4 mole-% moisture feed. Each catalyst was run under these conditions for about 500 hrs. Over the next 500 hrs., the butane concentration to each reactor was increased to 2.4% at GHSV values of 1600 to 1650/hr. Butane conversions were in the range from 76 to 85%. Each reactor reached steady state operation over the next 500 to 1000 hrs. of on-stream time. Table 6 records the reactor operating conditions for catalyst nos. 4 and 12 at times when each reactor had nearly equal conversions of the 2.4% butane feed. As can be seen from the data, the Bi-promoted catalyst no. 12 operates at bath temperatures of 15° to 20° C. lower than the unpromoted catalyst no. 4 and shows a lower hot spot than the unpromoted catalyst. The advantages of such operation (lower bath and hot spot temperatures) include longer life and better control of hot spot runaways at high butane feed concentrations.

TABLE 7[a]

| CAT. NO., PROMOTER | OST, HR | BATH °C. | HS-RX (°C.) | %-CNV | %-SEL | %-YLD | % C Tls |
|---|---|---|---|---|---|---|---|
| 4,None | 1973 | 428 | 458 | 84.6 | 70.3 | 59.0 | 99.3 |
| 12,Bi | 1569 | 409 | 438 | 84.9 | 70.3 | 59.2 | 99.3 |

(Bi/V = 0.01)
[a]Conditions: GHSV = 1600 to 1625/hr., inlet pressure = 29 to 31 psig, feed stream moisture = 2.2 to 2.6 mole-%, feed stream OP(OCH$_3$)$_3$ = 19 to 20 ppm.

EXAMPLE 11

In the description of the preferred embodiments of this invention, the vanadyl pyrophosphate phase that forms during treatment of the catalyst tablets in a butane/oxygen gas mixture is characterized as preferably having a peak height intensity ratio that is less than about 1.20 for the powder X-ray diffraction d-spacings at 3.86 and 3.14 Å. Catalysts of this invention typically are prepared in alcoholic solutions that afford a poorly crystalline solid precursor catalyst. When the precursor catalyst is activated in an air/nitrogen/steam atmosphere, the precursor phase is converted into a primarily vanadyl pyrophosphate phase. Equilibration of this (VO)$_2$P$_2$O$_7$ phase in a butane/oxygen gas mixture leads to further crystallization of the (VO)$_2$P$_2$O$_7$ phase. Five butane/oxygen equilibrated catalysts are tabulated below. The last entry in this tabulation represents a reactor equilibrated (VO)$_2$P$_2$O$_7$ phase made from aqueous solution. A portion of that equilibrated catalyst was further crystallized in a Parr bomb which was heated to 450° C. for four hours. A light green solid was recovered and the powder X-ray diffraction pattern recorded. The peak intensities are listed for the last entry below designated as catalyst no. 22.

TABLE 8

| Cat. No. | Promoter M | M/V | d-spacing Peak Intensities 3.86Å | d-spacing Peak Intensities 3.14Å | Ratio of 3.86Å/3.14Å Intensities |
|---|---|---|---|---|---|
| 1C | Zr | 0.01 | 148 | 155 | 0.955 |
| 1D | Zr | 0.02 | 171 | 156 | 1.096 |
| 4 | None | 0.00 | 156 | 153 | 1.020 |
| 12 | Bi | 0.01 | 166 | 151 | 1.099 |
| 16 | Sn | 0.01 | 143 | 144 | 0.993 |
| 22 | None | 0.00 | 676 | 459 | 1.473 |

What is claimed is:

1. An active, phosphorus vanadium oxide catalyst for the conversion to maleic anhydride of a non-aromatic hydrocarbon having at least four carbon atoms in a straight chain, said catalyst comprising a shaped body having a volume of at least about 0.02 cc, and having been equilibrated to provide a developed surface area of at least about 28 m$^2$/g, said catalyst containing a promoter selected from the group consisting of bismuth, antimony, germanium, titanium, zirconium, cerium, lanthanum, uranium, nickel, zinc, tin, silicon, and mixtures thereof, in such a proportion as to enable the catalyst to have said developed surface area and to exhibit a weight/area productivity of at least about 3.5 mg maleic anhydride/m$^2$-hr and/or a weight/weight productivity of at least about 100 g maleic anhydride/kg.cat.-hr. when contacted with a gas containing 2.4% by volume n-butane in air, at a gas flow volume to catalyst weight ratio of 2180 cc/g-min. under a pressure of $1.055 \times 10^2$-kPa-G, and at a temperature sufficient to maintain a hydrocarbon conversion of 85 mole percent.

2. A catalyst as set forth in claim 1 wherein the molar ratio of said promoter to vanadium is between about 0.005 and about 0.04.

3. A catalyst as set forth in claim 2 wherein the molar ratio of said promoter to vanadium is between about 0.007 and about 0.02.

4. A catalyst as set forth in claim 3 wherein the molar ratio of the sum of all promoter elements to vanadium is not greater than about 0.04.

5. A catalyst as set forth in claim 1 wherein said promoter is selected from the group consisting of zirconium and bismuth.

6. A catalyst as set forth in claim 5 containing a bismuth promoter in a ratio of between about 0.007 and about 0.015 moles/mole vanadium.

7. A catalyst as set forth in claim 1 wherein said promoter is selected from the group consisting of nickel, zinc, lanthanum, cerium, and tin.

8. A catalyst as set forth in claim 1 wherein said promoter is selected from the group consisting of antimony, germanium, titanium, uranium, and silicon.

9. A catalyst as set forth in claim 1 wherein said shaped body has a volume of at least about 0.03 cc.

10. A catalyst as set forth in claim 1 wherein said shaped body has a volume of at least about 0.05 cc.

11. A catalyst as set forth in claim 1 having an X-ray diffraction pattern wherein the ratio of the peak height at a d-spacing of about 3.86 angstroms to the peak height at a d-spacing of about 3.14 angstroms is between about 0.8 and about 1.3.

12. An active phosphorus vanadium oxide catalyst where the conversion of a C$_4$ hydrocarbon to maleic anhydride comprising a fixed bed of shaped bodies, the catalyst bodies of said fixed bed having an average volume of at least about 0.02 cc, the catalyst having been equilibrated to provide a developed surface area of at least about 28 m$^2$/g, and containing a promoter selected from the group consisting of bismuth, antimony, germanium, titanium, zirconium, lanthanum, cerium, uranium, nickel, zinc, tin, silicon, and mixtures thereof, in such a proportion as to enable the catalyst to have said developed surface area and to exhibit a weight/area productivity to maleic anhydride of at least about 3.5 mg maleic anhydride/m$^2$-hr and/or a weight/weight productivity of at least about 100 g maleic anhydride/kg.cat.-hr. when contacted with a gas containing 2.4% n-butane in air, at a gas flow volume to catalyst weight ratio of 2180 cc/g-min. under a pressure of $1.055 \times 10^2$-kPa-G, and at a temperature sufficient to maintain the hydrocarbon conversion of 85 mole percent.

13. An active equilibrated catalyst as set forth in claim 12 wherein the average volume of said shaped bodies is at least about 0.03 cc.

14. A catalyst as set forth in claim 13 wherein the average volume of said shaped body is at least about 0.05 cc.

15. A catalyst as set forth in claim 12 wherein said promoter is selected from the group consisting of zirconium and bismuth.

16. A catalyst as set forth in claim 12 wherein said promoter is selected from the group consisting of nickel, zinc, cerium, lanthanum, and tin.

17. A catalyst as set forth in claim 12 wherein said promoter is selected from the group consisting of antimony, germanium, titanium, uranium, and silicon.

18. A catalyst as set forth in claim 12 having an X-ray diffraction pattern wherein the ratio of the peak height at a d-spacing of about 3.86 angstrom to the peak height at a d-spacing of about 3.14 angstrom is between about 0.8 and about 1.3.

19. An active phosphorus vanadium oxide catalyst comprising a shaped body having a volume of at least about 0.02 cc and containing a zirconium promoter in a ratio of between about 0.005 and about 0.04 moles zirconium per mole vanadium.

20. An active phosphorus vanadium oxide catalyst comprising a shaped body having a volume of at least about 0.02 cc and containing a bismuth promoter in a ratio of between about 0.007 and about 0.015 moles bismuth per mole vanadium.

21. An active phosphorus vanadium oxide catalyst in the form of a shaped body exhibiting a volume of at least about 0.02 cc, a developed surface area of at least about 28 m²/g, said catalyst containing a promoter selected from the group consisting of bismuth, antimony, germanium, titanium, zirconium, lanthanum, cerium, uranium, zinc, nickel, tin, silicon, and mixtures thereof in a proportion effective to cause the catalyst to exhibit a weight/area productivity of at least about 3.5 mg maleic anhydride/m²-hr and/or a weight/weight productivity of at least about 100 g maleic anhydride/kg cat.-hr when contacted with a gas containing 2.4% by volume n-butane-in-air, at a gas flow volume to catalyst weight ratio of 2180 cc/g-min under a pressure of $1.055 \times 10^2$ kPa-G, and a temperature sufficient to maintain a hydrocarbon conversion of 85 mole percent, and corresponding to the formula $$(VO)_2(M)_m P_2 O_7 \cdot b(P_{2/c}O)$$

wherein M comprises a promoter as defined above, m is a number from about 0.005 to about 0.04, b is a number taken to provide a P/V atom ratio of from about 0.95 to about 1.3, c is a number representing the oxidation number of phosphorus and has a value of 5, said catalyst having a crystal structure corresponding to that of a catalyst that has been activated by a process comprising the steps of:

(a) heating a catalyst precursor composition in an atmosphere selected from the group consisting of air, steam, inert gas, and mixtures thereof, to a temperature not to exceed 300° C., said catalyst precursor composition corresponding to the formula $$VO(M)_m HPO_4 \cdot aH_2O \cdot b(P_{2/c}O) \cdot n(\text{organics})$$

wherein M, m, b, , and c are as defined above, a is a number of at least about 0.5, and n is a number taken to represent the weight % of intercalated organics component;

(b) maintaining the catalyst precursor at the temperature of Step (a) and providing an atmosphere containing molecular oxygen, steam, and optionally an inert gas, the atmosphere being represented by the formula $$(O_2)_x (H_2O)_y (IG)_z$$

wherein IG is an inert gas and x, y, and z represent mol percent of the $O_2$, $H_2O$, and IG components, respectively, in the molecular oxygen/steam-containing atmosphere, with x having a value greater than zero (0) mol %, but less than 100 mol %, y having a value greater than zero (0) mol %, but less than 100 mol %, and z having a value representing the balance of the molecular oxygen/steam-containing atmosphere;

(c) increasing the temperature at a programmed rate of from about 2° C./min to about 12° C./min to a value effective to eliminate the water of hydration from the catalyst precursor;

(d) adjusting the temperature from Step (c) to a value greater than 350° C., but less than 550° C. and maintaining the adjusted temperature in the molecular oxygen/steam-containing atmosphere for a time effective to provide a vanadium oxidation state of from about +4.0 to about +4.5; and (e) continuing to maintain the adjusted temperature in a nonoxidizing, steam-containing atmosphere for a time effective to complete the catalyst precursor to active catalyst transformation to yield the active catalyst.

* * * * *